United States Patent [19]

Paul et al.

[11] Patent Number: 5,320,102
[45] Date of Patent: Jun. 14, 1994

[54] METHOD FOR DIAGNOSING PROTEOGLYCAN DEFICIENCY IN CARTILAGE BASED ON MAGNETIC RESONANCE IMAGE (MRI)

[75] Inventors: Pradip K. Paul, Cranford; Mukundrai K. Jasani, Berkeley Heights; Elizabeth O'Byrne, Millburn; Douglas Wilson, Scotch Plains; Ashok Rakhit, Berkeley Heights, all of N.J.

[73] Assignee: Ciba-Geigy Corporation, Ardsley, N.Y.

[21] Appl. No.: 978,511

[22] Filed: Nov. 18, 1992

[51] Int. Cl.$^5$ ............................................. A61B 5/055
[52] U.S. Cl. .................................................. 128/653.2
[58] Field of Search ....................... 128/653.2; 436/173

[56] References Cited

U.S. PATENT DOCUMENTS 5,206,023  4/1993  Hunziker ........................... 424/423

OTHER PUBLICATIONS

"Magnetic Resonance Imaging Reflects Cartilage Proteoglycan Degradation in the Rabbit Knee", Pradip K. Paul et al., Skeletal Radiol., (1991), 20:31–36.
"Intevertebral Disk: Normal Age-related Changes in MR Signal Intensity[1]", Lowel A. Sether et al., Neuroradiology, Nov. 1990, pp. 385–388.
"RSNA'89 Scientific Program", Radiological Society of North America, Nov. 26–Dec. 1, Chicago, p. 436.
"MRI Evaluation of Early Degenerative Cartilage Disease by a Three-dimensional Gradiaent Echo Sequence", K. Glückert et al., Tissue Characterization in MR Imaging, pp. 185–192.
"Articular Cartilage: Correlation of Histologic Zone with Signal Intensity at MR Imaging", Jean M. Modi et al., Radiology, 1991, pp. 853–855.
"Structure, Function, and Degeneration of Bovine Hyaline Cartilage: Assessment with MR Imaging in Vitro[1]", Radiology, 1989, pp. 495–499.
"Anatomical Changes and Patheogenesis of OA in Man, with Particular Reference to the Hip and Knee Joints", D. L. Gardner et al., pp. 22–48.
"Biochemical Changes in Human Osteoarthrotic Cartilage", M. T. Bayliss, pp. 50–56.

*Primary Examiner*—Ruth S. Smith
*Attorney, Agent, or Firm*—Wenderoth, Lind & Ponack

[57] ABSTRACT

Proteoglycan deficiency in articular cartilage is diagnosed based on quantified signal intensities of pixels of a magnetic resonance image (MRI) extending across a depth of the articular cartilage. A pattern of the thus quantified signal intensities is indicative of proteoglycan distribution across the cartilage depth.

24 Claims, 18 Drawing Sheets

—●— AVG LAT TIB INT —■— AVG MED TIB INT

MEAN FOR ALL SUBJECTS

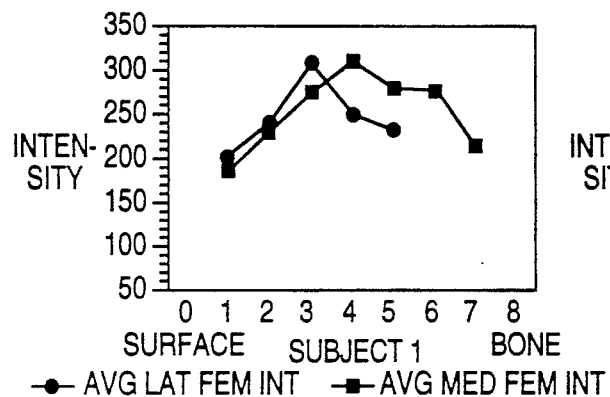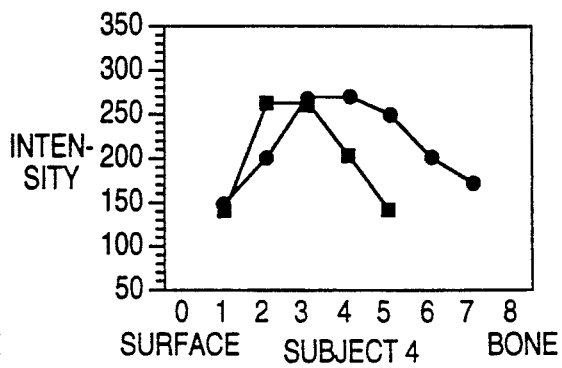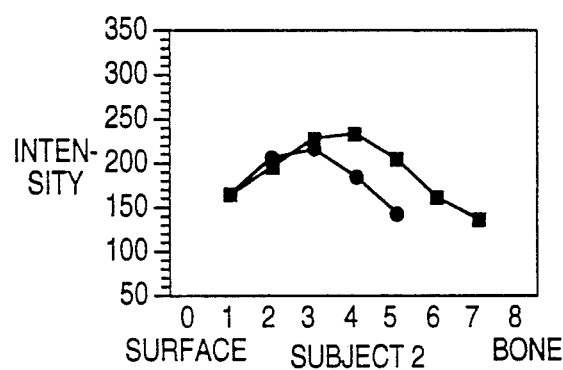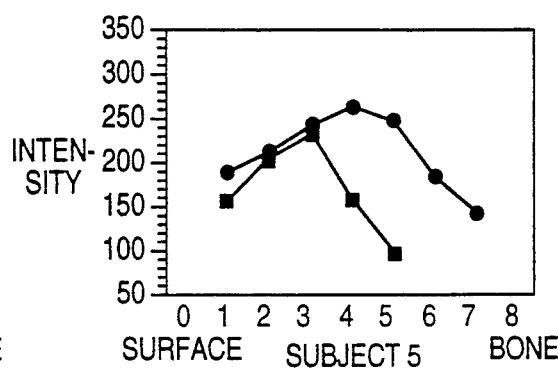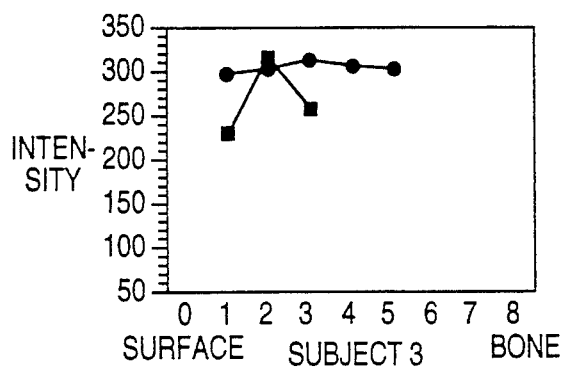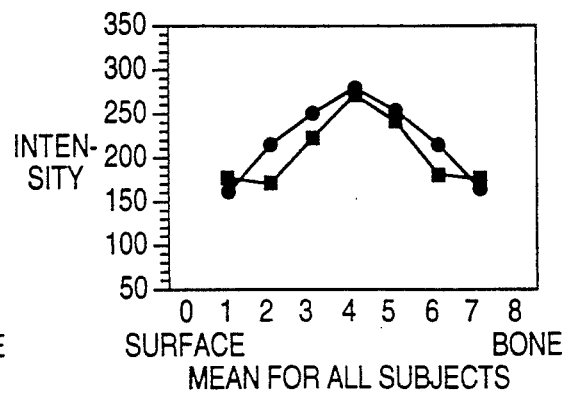

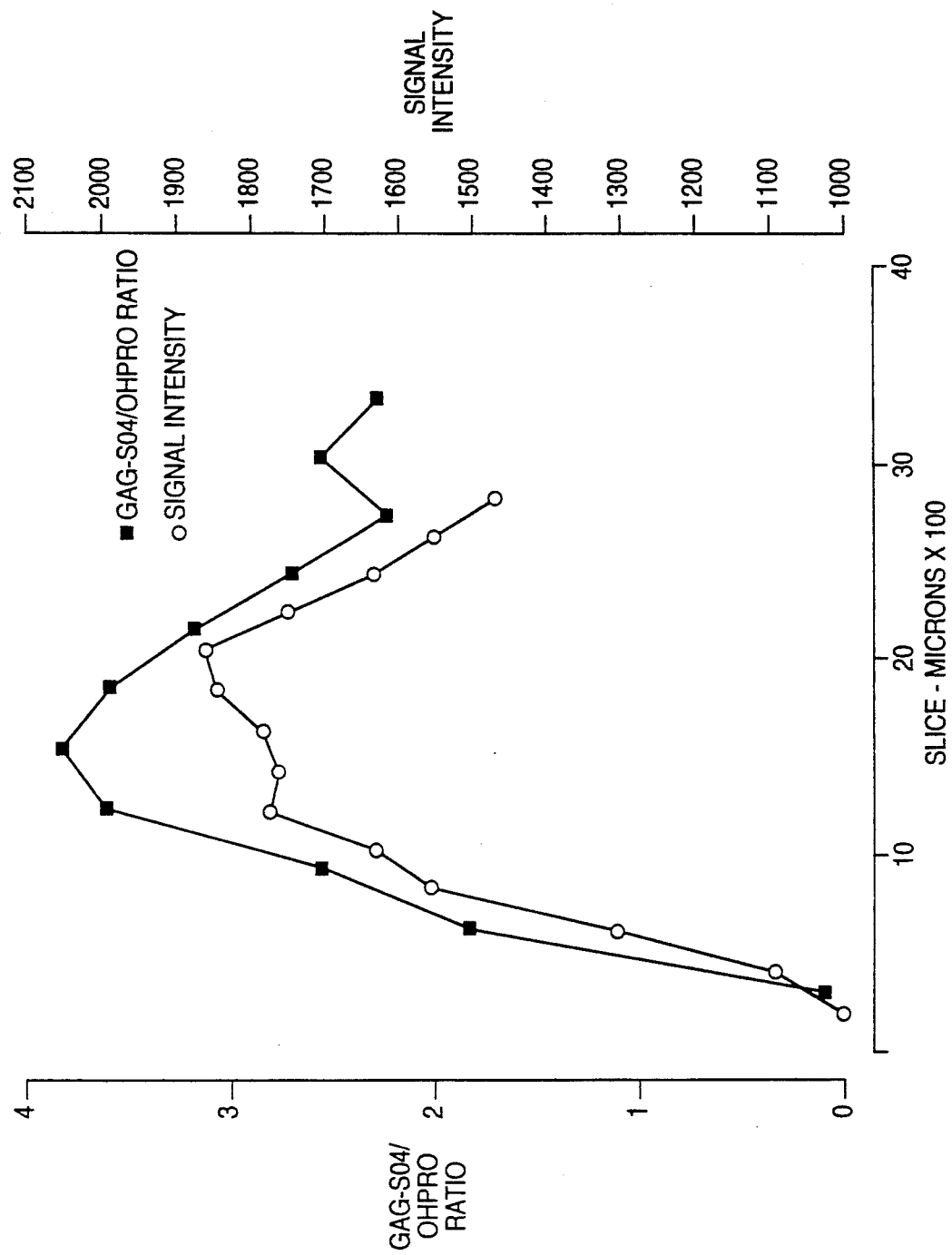

COMPARISON OF PEAK INTENSITY IN FEMORAL AND TIBIAL CARTILAGES OF 7 RA PATIENTS WITH 5 NORMAL VOLUNTEERS

FEMORAL

| SUBJECT | RA MEDIAL | RA LATERAL | | SUBJECT | NORMAL MEDIAL | NORMAL LATERAL |
|---|---|---|---|---|---|---|
| 1 | 17.70 | 22.80 | | 1 | 154.65 | 157.30 |
| 2 | 176.10 | 147.70 | | 2 | 118.30 | 210.70 |
| 3 | 17.80 | 14.65 | | 3 | 197.85 | 196.35 |
| 4 | 21.15 | 21.50 | | 4 | 135.10 | 134.80 |
| 5 | 22.75 | 22.90 | | 5 | 159.07 | 186.70 |
| 6 | 24.80 | 30.60 | | 6 | 193.95 | 192.54 |
| 7 | 21.60 | 25.15 | | | | |
| AVERAGES: | 43.13 | 40.76 | | AVERAGES: | 159.82 | 179.73 |
| STD: | 58.69 | 47.39 | | STD: | 31.54 | 28.18 |
| STD ERROR: | 22.18 | 17.91 | | STD ERROR: | 12.88 | 11.50 |
| | | | | % DIFF: | -73.01 | -77.32 |
| | | | | T-TEST: | 0.0012 | 0.0001 |
| | | | | M-W EQUIV: | 0.0076 | 0.0005 |

RA & NORMAL COMPARISONS

TIBIAL

| SUBJECT | RA MEDIAL | RA LATERAL | | SUBJECT | NORMAL MEDIAL | NORMAL LATERAL |
|---|---|---|---|---|---|---|
| 1 | 17.85 | 19.50 | | 1 | 132.55 | 133.90 |
| 2 | 94.00 | 209.90 | | 2 | 203.45 | 209.35 |
| 3 | 15.30 | 10.95 | | 3 | 187.80 | 172.85 |
| 4 | 21.80 | 17.75 | | 4 | 129.40 | 120.65 |
| 5 | 17.55 | 18.80 | | 5 | 115.30 | 182.20 |
| 6 | 19.60 | 26.05 | | 6 | 145.50 | 146.50 |
| 7 | 19.35 | 22.45 | | | | |
| AVERAGES: | 29.35 | 46.49 | | AVERAGES: | 152.33 | 160.91 |
| STD: | 28.58 | 72.21 | | STD: | 35.23 | 33.17 |
| STD ERROR: | 10.80 | 27.29 | | STD ERROR: | 14.38 | 13.54 |
| | | | | % DIFF: | -80.73 | -71.11 |
| | | | | T-TEST: | 0.001 | 0.0045 |
| | | | | M-W EQUIV: | 0.0001 | 0.0242 |

RA & NORMAL COMPARISONS

*FIG. 11*

METHOD FOR DIAGNOSING PROTEOGLYCAN DEFICIENCY IN CARTILAGE BASED ON MAGNETIC RESONANCE IMAGE (MRI)

BACKGROUND OF THE INVENTION

1. Field of the Invention

This invention relates to the diagnosis of proteoglycan deficiency in articular cartilage based on magnetic resonance images (MRI) of the articular cartilage, and more particularly, based on a quantified signal intensity of each pixel of the magnetic resonance image extending across a depth of the articular cartilage.

2. Description of the Related Art

In magnetic resonance imaging (MRI), which is widely used for diagnostic purposes in medicine, a large magnet supported by complicated electronics and computers is employed for image acquisition. When a patient is made to lie in the magnet's magnetic field, individual atoms within the patient's tissues and organs become aligned with the magnetic field. Radiofrequency pulses are then transmitted at a defined rate to the magnetized atoms in the area of interest to thereby elevate the energy levels in the atoms. During a pause period between pulses, the atoms relax and part of the energy gained becomes released. This process represents the unique phenomenon of magnetic resonance. A receiving antenna collects the released energy signals which are then subjected to image processing to convert the energy signals into light dots (pixels) having an illumination level (e.g. a gray-scale) corresponding to an intensity of the energy signals. Thousands and thousands of such light dots form an image. The thus obtained MR image is displayed on a television monitor, printed as a hard copy image and/or stored on a magnetic tape or other recording medium.

An MR image provides structural information, such as size and shape, regarding most tissues and organs in the body, and permits the visual detection of changes in such structural characteristics. For example, if a person develops a meniscal or anterior cruciate ligament tear as a result of a sports related injury, an MRI of the joint will reveal the presence of a discontinuity, swelling and/or shortening in the image of the torn tissue. The structural image information provided by the MRI helps to decide whether a patient requires surgical repair or other remedial action.

FIG. 1 is a parasagittal section view (lateral to midline) of the human knee joint. Reference numeral 101 denotes the femur; 102 denotes the articularis genus muscle; 103 denotes the quadriceps femoris tendon; 104 denotes 104 denotes the suprapatellar fat body; 105 denotes the suprapatellar synovial bursa; 106 denotes the patella; 107 denotes the subcutaneous prepatellar bursa; 108 denotes the articular cavity; 109 denotes the infrapatellar fat body; 110 denotes the patellar ligament; 111 denotes the synovial membrane; 112 denotes the subcutaneous infrapatellar bursa; 113 denotes the deep (subtendinous) infrapatellar bursa; 114 denotes the lateral meniscus; 115 denotes the tuberosity of tibia; 116 denotes the bursa under lateral head of gastrocnemius muscle; 117 denotes the synovial membrane; 118 denotes the articular cartilages; and 119 denotes the tibia. Articular cartilage covers the opposing femur and tibia bone ends in the human knee joint. The articular cartilage, which is rich in extracellular matrix and poor in cellularity, has shock absorption and lubrication functions based on its visco-elasticity which depends on the high water content of its extracellular matrix. Normal human articular cartilage has a water content of 73%-81% (w/w) on a weight basis. Proteoglycans (PG) are the vital organic component required for the functions of articular cartilage. PG contains numerous sugar chains, namely glycosaminoglycans, which contain negatively charged groups such as carboxylates and sulfate groups. These water absorbing, i.e. hydrophilic, groups attract an excess of water hydrogen atoms and water carrying cations. The wide spread network of PG retains this water in the cartilage matrix. A decrease in PG causes changes in the amount and state of water contained therein, resulting eventually in cartilage dysfunction. Thus a PG depletion is indicative of cartilage degeneration and precedes such problems as osteoarthritis.

Although the MRI is used to visually detect structural changes in the articular cartilage of post-trauma joints, currently no non-invasive diagnostic tool is available to detect a biochemical change such as PG depletion in the articular cartilage at very early stages of cartilage degradation. Detection of PG depletion in cartilage prior to a structural change taking place could be extremely beneficial because steps could be initiated to preserve the cartilage by therapeutic intervention. Once PG depletion has started, the surface of the cartilage begins to break after 1-2 years (fibrillation). As a result of fibrillation, usually in about 5 years the cartilage becomes thinned resulting in a narrowing of the joint space. Therefore any attempt to protect or preserve the cartilage must be made before initiation of surface breaking.

Present techniques employing MRI are not capable of detecting biochemical changes, particularly PG depletion, that develop in articular cartilage following joint trauma several years in advance of structural disorganization referred to as osteoarthritis (OA).

SUMMARY OF THE INVENTION

An object of the present invention is to provide a non-invasive method employing quantitative techniques for diagnosing a proteoglycan deficiency in articular cartilage, preferably prior to the onset of fibrillation and structural disorganization.

Another object of the invention is to provide a non-invasive method for tracking the progression or remission of proteoglycan depletion in articular cartilage which would be useful, for example, in a cartilage preserving drug development/screening program.

Another object of the invention is to provide a non-invasive method for diagnosing an arthritic joint.

In achieving the above and other objects, the method of this invention includes quantifying a signal intensity of a magnetic resonance image of the cartilage and correlating the thus quantified signal intensity with at least one predetermined reference signal intensity indicative of cartilage proteoglycan content, e.g. with an expected or normal peak signal intensity indicative of an expected or normal proteoglycan content, or with an expected or normal signal intensity pattern indicative of an expected or normal proteoglycan concentration across cartilage depth.

Generally, the MRI signal intensity is quantified across the depth of the cartilage as a gray-scale illumination of pixels of the image. The signal intensity variation across the depth of the cartilage is correlated with an expected or normal bell-shaped variation. Also, a peak signal intensity in a middle portion of the cartilage is compared with predetermined reference signal intensities indicative of expected or normal PG content.

Further, the signal intensity within a same pixel layer of the cartilage may be analyzed, and a comparison of signal intensity variation in the medial vs. lateral condyles may be carried out.

BRIEF DESCRIPTION OF THE DRAWINGS

The object and features of this invention will become clear in the detailed description that follows with reference to the accompanying drawings in which:

FIGS. 6(a) through 6(f) illustrate the signal intensities across cartilage depth seen in images of the medial and lateral femoral condyles for the five healthy volunteers and the mean for all healthy volunteers;

FIG. 10 illustrates the signal intensity across the depth of human articular cartilage and the proteoglycan content across the depth of the same cartilage;

FIG. 11 is a table comparing the peak intensity from femoral and tibial cartilage of seven rheumatoid arthritis patients and five healthy volunteers; and, FIGS. 12(a) and 12(b) through FIGS. 18(a) and 18(b) respectively illustrate the signal intensity curve across the femoral cartilage and the signal intensity across the tibial cartilage of the seven rheumatoid arthritis patients.

DETAILED DESCRIPTION OF THE PREFERRED EMBODIMENTS

Figure 1:
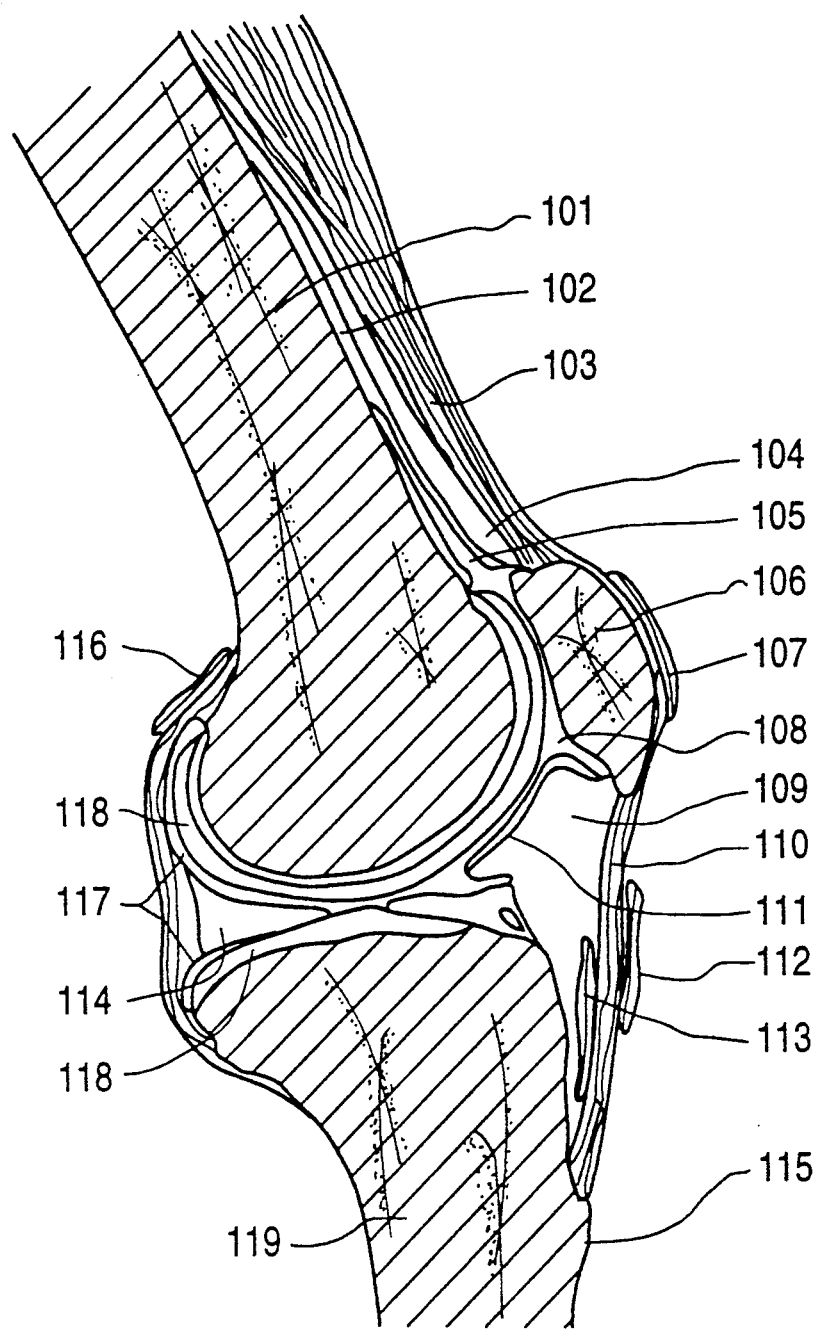
FIG. 1 is a parasagittal section view (lateral to midline) of the human knee joint.

Previous research of the present inventors has shown that the cartilage thickness measurable on magnetic resonance images of rabbit knee cartilage, obtained using spin echo pulse sequences with TR=1000 msec and TE=30 msec, correlated well with changes in the proteoglycan content brought about by intraarticular injection of the plant-derived proteolytic enzyme papain. (See Paul et al., "Magnetic Resonance Imaging Reflects Cartilage Proteoglycan Degradation in the Rabbit Knee", Skeletal Radiol, 1991.)

Such injection of papain is known to profoundly deplete the cartilage proteoglycan content, but the process following a single injection is known to be reversed through increased synthesis by the chondrocytes which returns the cartilage proteoglycan content toward normality. In the inventors' experiments in connection with the above-mentioned previous research, the depletion of proteoglycan content appeared to correlate with a decrease, and the repletion with an increase, in the cartilage thickness which was measured using the MR image.

Since changes in cartilage thickness coincided with comparable changes in the measurable signal intensity, a quantitative MRI technique was developed and applied to healthy human knees to investigate whether the MRI signal intensity is truly related to the proteoglycan content. The goal was to quantify the signal intensity of all pixels in a particular region of the knee cartilage using computer-based image analysis. This was done in order to assess whether the signal intensity varied across the cartilage depth, and whether such variations correspond with the distribution of any of the three major biochemical constituents of cartilage, i.e. water, collagen and proteoglycans, known to be differentially distributed across the cartilage depth.

Six healthy volunteers ranging in age from 20–40 years old were studied. The right knee joint of each individual was scanned using a 1.5T (Signa, Ge, Milwaukee, Wis.) magnet and a dedicated transmit/receive extremity coil with the subject laying in the supine position. Three series of images were obtained in 5 of the 6 subjects, two using spin echo (SE) pulse sequences with TR msec/TE msec=700/20 and 1000/20. The third series was obtained using gradient refocused echo (GRE) 3D volume acquisition (60/15) and a flip angle of 15°. This pulse sequence was chosen since it reduces the scanning time while improving cartilage image contrast. The sixth subject was studied using only the GRE pulse sequence as explained below but using three different flip angles to further evaluate the signal intensity variation in cartilage images.

For the spin echo, a coronal localizer (500/20) was followed by two sagittal acquisitions using first 700/20 and then 1000/20 pulse sequences. Either an 8 or 12 cm FOV was used. Other parameters were as follows: slice thickness 4 mm and interslice gap 1.5 mm, matrix 256×256 and two averages (in plane resolution 300 and 450 microns). For the GRE sequence, the same FOV and plane were used. Twenty-eight to sixty contiguous slice locations were obtained using either 1.5 m or 3 mm slice thicknesses (in plane resolution 300 and 450 microns). Other parameters were kept similar for all the 5 subjects studied. Finally, to further determine the degree of T1 weighted dependence of the signal intensity, in the sixth subject the knee was imaged using only the GRE sequence, but at 15°, 30°, and 50° flip angles.

For each study, femoral and tibial cartilage images obtained in the sagittal plane were analyzed on a Sun Sparc 1+workstation (Sun Microsystems, Saddle Brook, N.J.) using modified image display computer software that permitted x16 magnification of the MR cartilage image, and allowed measurement of the signal intensity on a pixel-by-pixel basis both across and along the full depth of the cartilage image.

Figure 2:
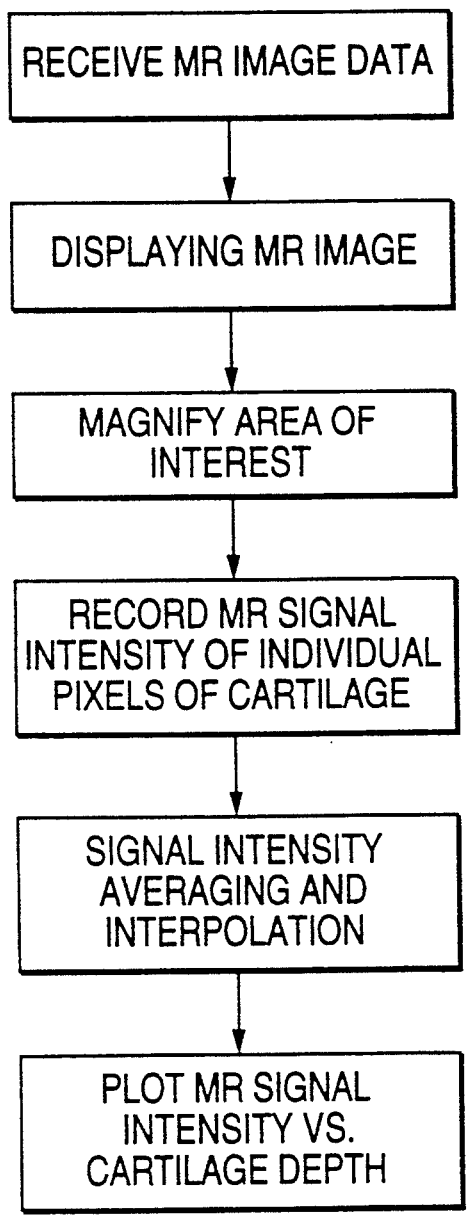
FIG. 2 is a process flow chart illustrating the image processing of a magnetic resonance image according to the present invention.

More particularly, reference is made to the imaging process flow chart of FIG. 2. As noted previously, the conventional MRI apparatus converts received signal intensities into image data denoting an illumination level of each pixel of the image corresponding to a location within the MRI slice or plane. This image data is received at the workstation (step 1) and displayed (step 2) in a conventional manner. Then, the operator chooses a window or area of interest (e.g. the femoral cartilage) within the display image. The chosen area is then magnified (step 3) for display. Responsive to user inputs individual pixels are selected (e.g by defining a region of interest within the overall magnified display image by tracing a boundary with the assistance of a computer mouse device), and the gray-scale illumination representative of the MR signal intensity of selected individual pixels is recorded (step 4). Then, as will be discussed in more detail below, the recorded signal intensities of the selected pixels are subjected to appropriate averaging and interpolation (step 5), for the purpose of plotting the signal intensity (y-axis) for each pixel along the depth (x-axis) of the cartilage (step 6).

Figure 3:
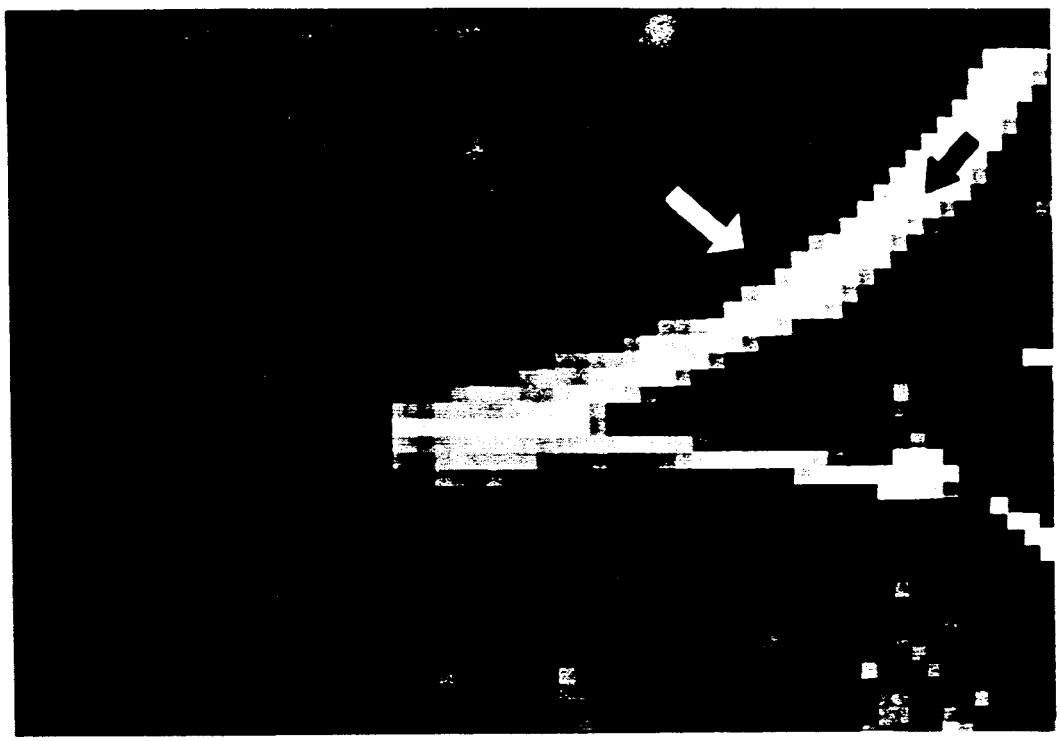
FIG. 3 is a femoral cartilage MR image at x16 magnification showing individual pixels in the cartilage depth.

In this manner, signal intensity was measured from the individual pixels of the femoral and tibial cartilage images. For example, FIG. 3 is a femoral cartilage image with x16 magnification showing individual pixels in the cartilage depth. The white arrow in FIG. 3 indicates a direction across the cartilage (i.e. a "depth direction"), and the black arrow indicates a direction along, i.e. within, each cartilage pixel layer. (The pulse sequence for the image obtained in FIG. 3 was GRE with $TR=60$ msec and $TE=15$ msec.)

Medial and lateral compartments were identified from anatomical and MR landmarks. Two mid-medial and two midlateral slices in the SE sequence, and five mid-medial and five mid-lateral slices in 3D volume GRE acquired cartilage images were analyzed. The region of the posterior femoral and tibial articular cartilages located above and below the middle third of a line connecting the base and the apex of the hypointense triangular shaped posterior horn of the medial and lateral meniscus was always analyzed. In each sagittal slice, signal intensity was measured from contiguous pixels along both the antero-posterior and supero-inferior planes (X and Y axes, respectively).

The data were processed to obtain the following:

1. Within pixel layer signal intensity variation (i.e. in the plane of the black arrow of FIG. 3): The differences between the signal intensity of 411 adjacent pairs of pixels were measured and statistically evaluated.

2. Across pixel layer signal intensity variation (i.e. in the plane of the white arrow of FIG. 3): To minimize errors from susceptibility artifacts, pixels at the edges near the bone and surface of the cartilage regions examined were excluded from the assessment. Secondly, since both the femoral and tibial cartilages have a curved geometry, the pixels are not oriented in a linear plane. Therefore, to facilitate the averaging process it was necessary to choose analysis of pixel columns containing either even or odd numbers of units. Odd numbers were selected, and columns containing even number of pixels were interpolated across the entire depth to an odd number. Thirdly, the signal intensity of 10 pixels present in the same row antero-posteriorly (black arrow, FIG. 3) was averaged to obtain the mean signal intensity value for each zone or pixel layer. Such measurements provided the inter-zonal or across the pixel layer signal variation curve in the cartilage region examined. This procedure was repeated in all of the medial and lateral slices studied.

3. Pixel layers and cartilage thickness. The number of pixel layers present across the depth of the cartilage was counted at each of the 10 sites. The average multiplied by the resolution of each pixel (e.g. 300 microns) provided a measure of cartilage thickness.

The measured signal intensities from images of medial and lateral compartments of femoral and tibial cartilages obtained in the subjects with the 3 pulse sequences noted above were compared.

Figure 4A:
FIGS. 4(a) through 4(c) illustrate MR images of a healthy knee obtained using two spin echo sequences and a GRE pulse sequence, respectively.
Figure 4B:
Figure 4C:
Figure 5A:
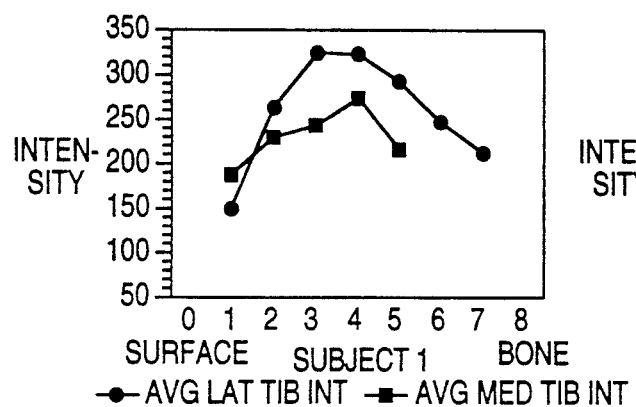
FIGS. 5(a) through 5(f) respectively illustrate the signal intensities across the cartilage depth seen in images of the medial and lateral tibial plateau for five healthy volunteers and the mean for all healthy volunteers.
Figure 5D:
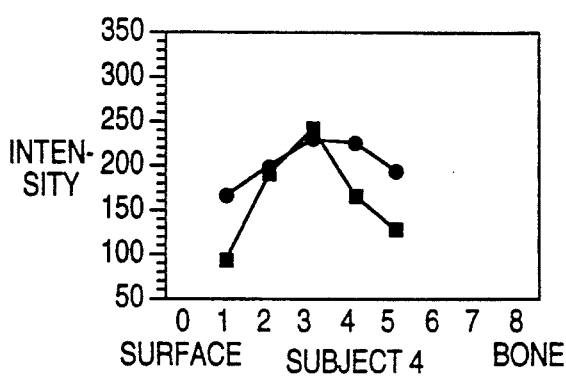
Figure 5B:
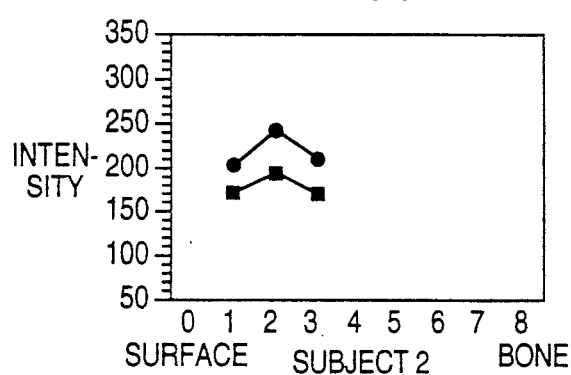
Figure 5E:
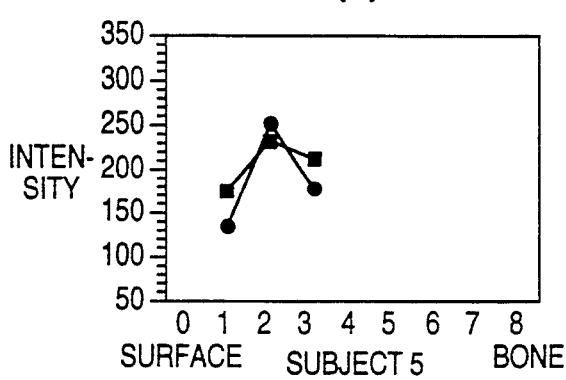
Figure 5C:
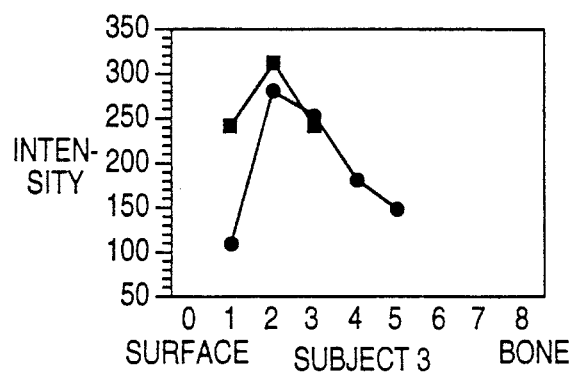
Figure 5F:
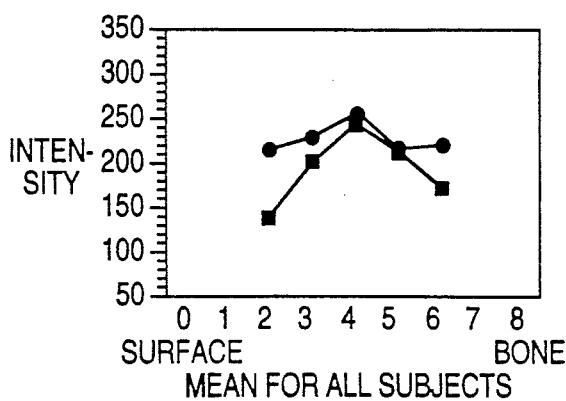

Typical mid-lateral sagittal images of the same region of the right knee obtained using the three pulse sequences are shown in FIGS. 4(a) through 4(c). More particularly, FIG. 4(a) is an MR image of a healthy knee obtained using a spin echo sequence $TR=1000$ msec and $TE=20$ msec, showing the meniscus, femoral and tibial cartilage in the sagittal plane. FIG. 4(b) is a similar view obtained using a spin echo sequence $TR=700$ msec and $TE=20$ msec. FIG. 4(c) is a similar view obtained using a GRE pulse sequence $TR=60$ msec and $TE=15$ msec. Compared with spin echo images, cartilage contrast was greater in the GRE images. Also, as can be seen from FIG. 3, a x16 magnified image showed differential contrast across but not within the pixel layers. Across the pixel layers the observed contrast was maximal in the middle and minimal at the surface and deep edges of the cartilage.

As noted previously, the signal intensity of each pixel in the region was measured to obtain the average pixel-by-pixel variation both across the pixel layers, i.e. along the cartilage depth, and within each pixel layer from a 10 pixel wide area measuring between 3 and 4.5 mm$^2$, depending upon the FOV used. Signal intensity within a pixel did not vary with magnification.

The results for images obtained using the spin echo 1000/20 sequence are described first in detail. Those for the other two sequences are then compared.

SPIN ECHO 1000/20

1. Pattern of Signal Intensity Variation

Within pixel layers. Signal intensity within each pixel layer was found to vary randomly. The median value for the differences between adjacent pairs of pixels equalled 7.0 (mean of 9.1 and mode of 5.0).

Across pixel layers. Across the pixel layers, the signal intensity varied by a significantly greater margin, by as much as 200.0. FIGS. 5(a) through 5(f) respectively illustrate the signal intensities across cartilage depth seen in images of the medial and lateral tibial plateau obtained using a spin echo 1000/20 pulse sequence for the five subjects and the mean for all subjects (mean differences between the signal intensities in cartilage zones 2 and 6 failed to be statistically significant). FIGS. 6(a) through 6(f) illustrate the same in images of the medial and lateral femoral condyles obtained using the spin echo 1000/20 pulse sequence. The signal intensity was maximal in pixel layers of the middle zone and minimal at both the superficial and deep edges. This resulted in the presence across the cartilage depth of a bell-shaped signal variation curve, which was present in all tibial and all except one out of ten femoral cartilages examined.

2. Peak Signal Intensity

The highest signal intensity was invariably present in pixel layers of the middle zone of the cartilage. In the medial compartment, the mean peak signal intensity was 250.5±44.2 (SD) and 272.4±39.7 for the tibial and femoral cartilages, respectively. The differences were not statistically significant. In the lateral compartment the mean peak signal intensity values were 264.8±39.1 and 275.3±38.6 for the tibial and femoral cartilages, respectively.

3. Number of pixel layers

The number of pixel layers varied as shown in FIGS. 5 and 6 between individuals and depending on both the FOV and the anatomic site. For example, in the tibial cartilage the number varied between 3 and 5 and in the femur between 3 and 9, irrespective of the compartment.

SPIN ECHO 700/20

The bell-shaped signal variation curve remained unchanged in all the subjects and in all the regions examined. The mean peak signal values for the tibial cartilages Were: 173.2±35.9 on the medial and 192.0±29.6 on the lateral side. Those for the femoral cartilages were: 219.8±24.8 on the medial and 207.8±29.0 on the lateral side. Without exception these values were significantly lower than the already stated corresponding values observed using the 1000/20 sequence (p<0.01 to 0.0001).

GRE 60/15

The signal variation curve was bell-shaped in all, including subject number 3 in whose lateral femoral cartilage the corresponding curves observed using the two spin echo sequences were flat.

The mean peak signal intensity values were the lowest. For example, in the tibial cartilages they were: 90.7±17.1 on the medial, and 86.2±9.7 on the lateral side. For the femoral cartilages they were: 98.8±11.8 on the medial, and 99.3±7.3 on the lateral side. Again without exception the differences between these and the corresponding results for the 1000/20 SE images were statistically significant (p<0.0002 to 0.0003).

Figure 7:
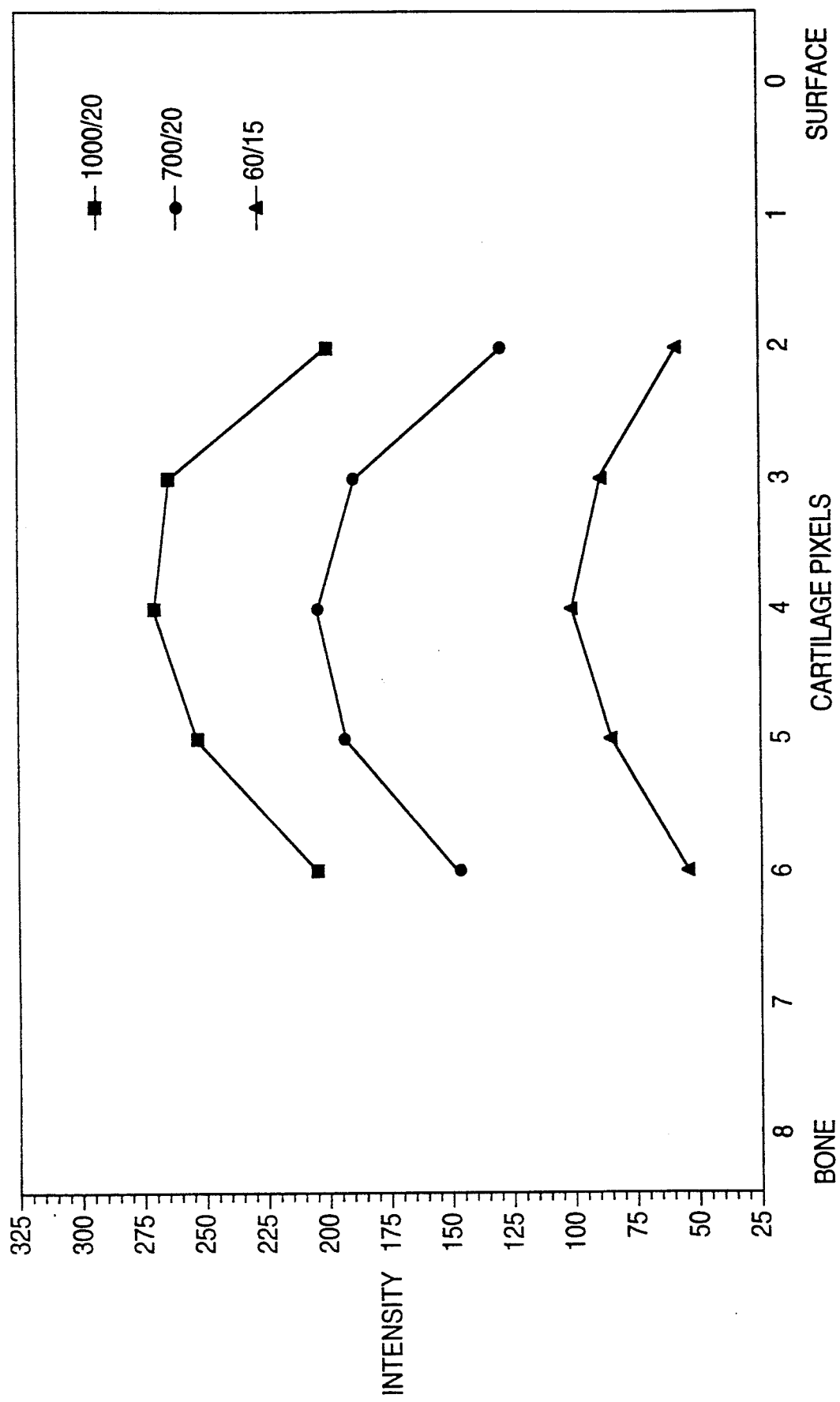
FIG. 7 illustrates the effect of changing the TR/TE of the MR image on signal intensities across cartilage depth seen on the images of the lateral femoral condyle of the right knee of one of the healthy volunteers.

FIG. 7 shows the effect of changing TR/TE from SE 1000/20 to either 700/20 or GRE 60/15 on signal intensities across cartilage depth seen on the images of the lateral femoral condyle of the right knee in subject 4. Results shown are the mean for all the slices obtained. Compared with 1000/20, the bell-shaped variation curve and the number of pixel layers seen on images obtained using the 700/20 pulse sequence remain unchanged, but there was a definite decrease in the signal intensity. The decrease occurred nearly uniformly across the cartilage depth. GRE resulted in an even greater decrease in signal intensity but, once again, the shape of its variation across the pixel layers remained virtually unchanged.

The results for the group of 5 subjects as a whole summarized below show that as compared with the 1000/20 findings, the peak cartilage signal intensity values observed using the 700/20 pulse sequence were intermediate and those using the GRE pulse sequences were the lowest.

Figure 8:
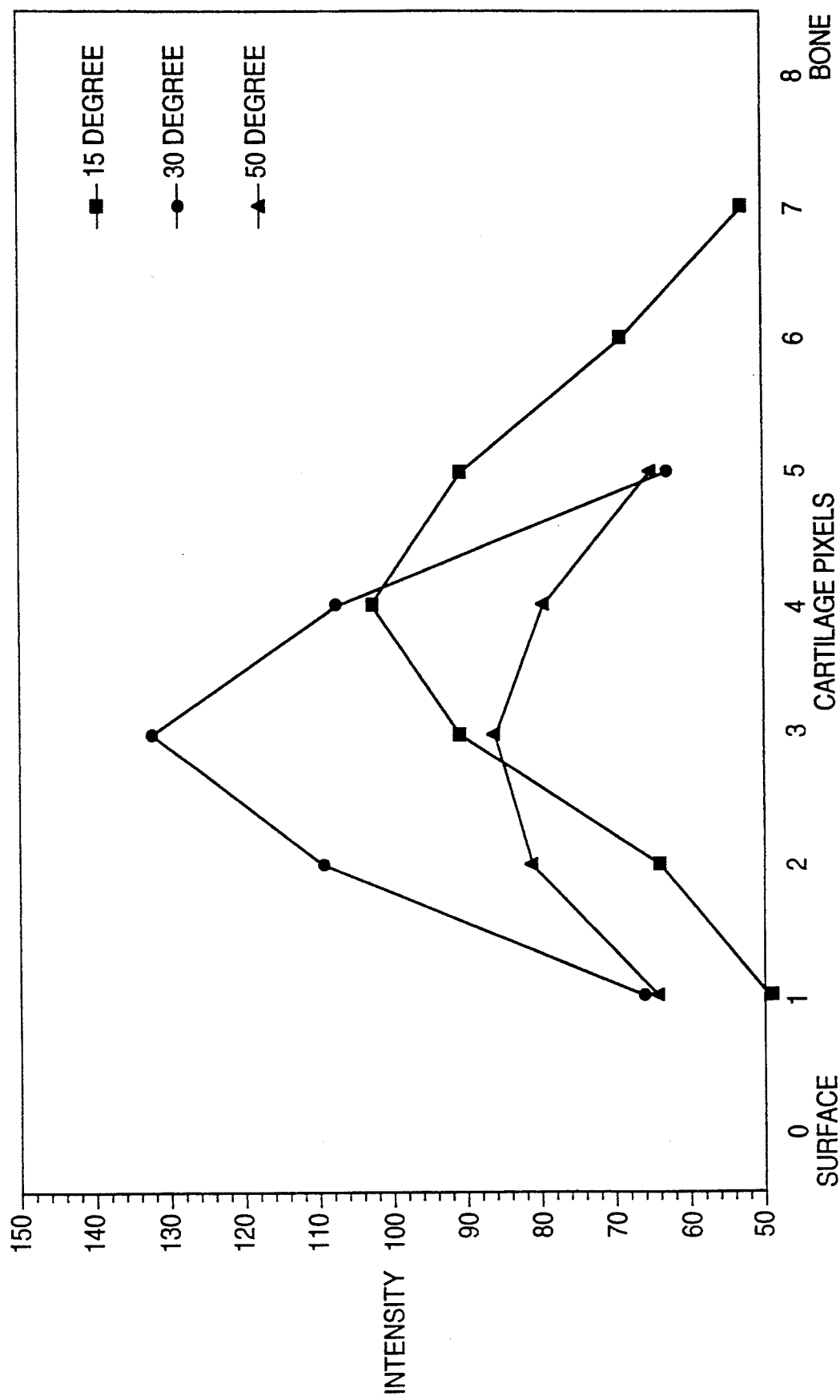
FIG. 8 illustrates the affect of changing the flip angle on signal intensities across cartilage depth seen on the image of the medial femoral condyle of the right knee of one of the healthy volunteers.

Changing the flip angle influenced the magnitude of signal intensity but not the shape of its variation curve. FIG. 8 shows the effect of changing the flip angle from 30° to either 15° or 50° on signal intensities across cartilage depth seen on the image of the medial femoral condyle of the right knee obtained using the GRE pulse sequence in subject 6. Results shown are the mean of all slices obtained. Changing the flip angle from the generally used 15° to 30° increased the peak signal intensity value by almost 30%, shifted the curve to the left, reduced the number of pixel layers by 2, but importantly left its bell-shaped form unchanged.

Further, an increase in the flip angle to 50° had the opposite effect. As can be seen from FIG. 8, the peak signal intensity value was decreased by nearly 15% compared to that observed with the 15° angle. The decrease was uneven across the cartilage depth. It was greatest in the pixels present in the middle layers and virtually nil in those at the cartilage periphery. The signal intensity curve was shifted to the right and the number of pixels were reduced by 2, although, once again, its outline remained essentially bell-shaped.

The data shows that the signal intensity seen on MR images of healthy human cartilage varied in a bell-shaped manner across, but not within, the pixel layers. The variation was found to be independent of magnification used, section location, anatomic site in the knee and even in the healthy individual examined.

Adjacent pixels within the same layer experience the same set of acquisition parameters including temperature and their biochemical composition is also likely to be comparable. This could explain why signal intensity variation within the pixel layers were found to vary only randomly and within a narrow range.

Findings for the medial and lateral compartments revealed that across the pixel layers the signal intensity varied by a significantly greater margin, by as much as 200.0. This resulted in the presence of a bell-shaped signal variation curve across both the femoral and tibial cartilages that was either identical or comparable in all except one subject.

The biochemical composition of cartilage varies across its depth. Therefore, MR signal intensity of pixels across the cartilage can be expected to vary too. However, this expectation has to be balanced against the question: to what extent is the bell-shaped signal variation due to technical factors associated with MR imaging? For reasons discussed below, the signal variations across pixel layers are judged to be intimately related to the biochemical factors, particularly PG content, rather than the possible influence of technical factors.

Figure 9:
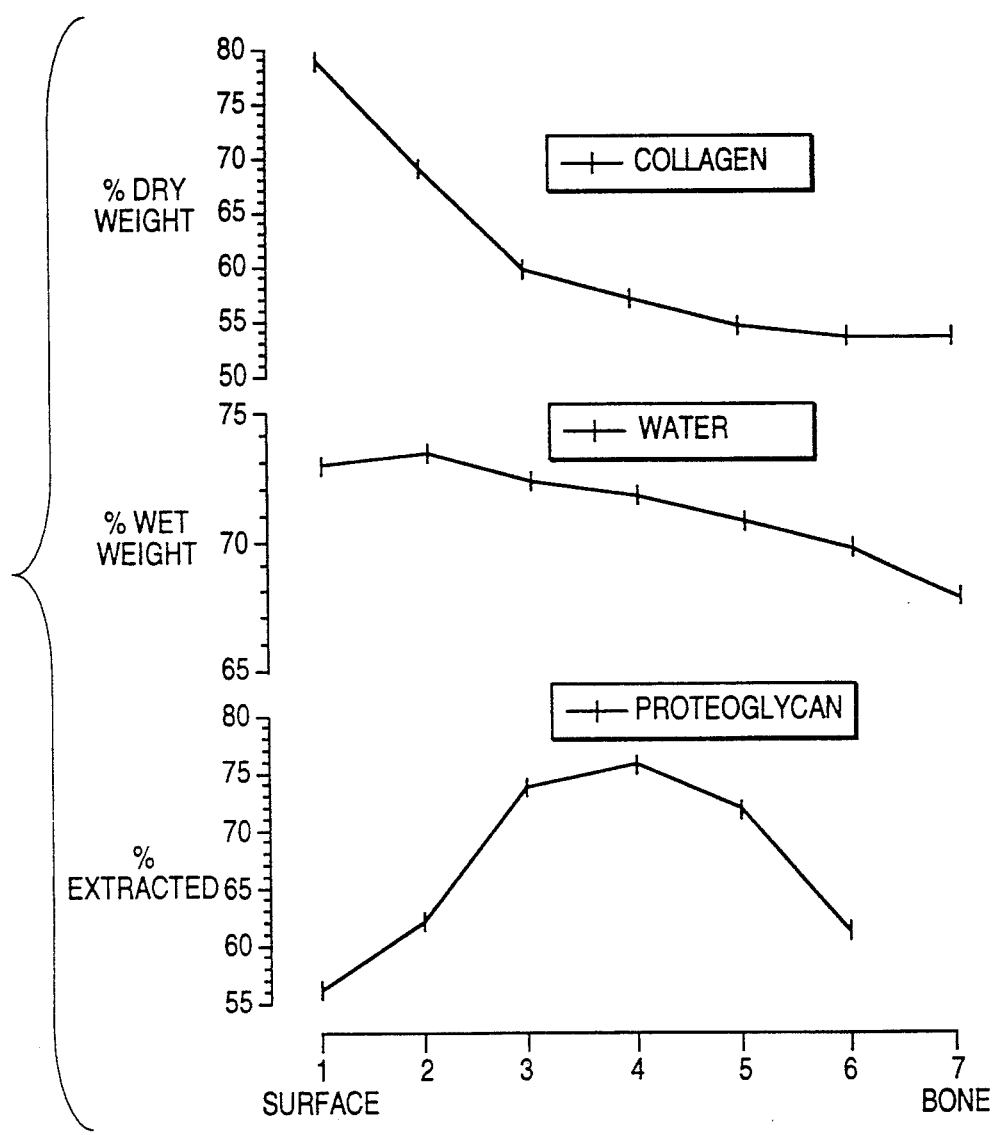
FIG. 9 illustrates variations in the distribution of collagen, water and proteoglycan content across the depth of normal human articular cartilage.

Biochemical data shows variations in the distribution of major matrix constituents across cartilage zone, but not within them, not at least in areas as small as examined in the present invention. Moreover, as shown in FIG. 9, the reported distribution of collagen, water, and proteoglycans shows the pattern of variation for each of them to clearly differ. Significantly, only the curve for the variation in the proteoglycan content is clearly bell-shaped and clearly similar to the curve for signal variation observed across the cartilage in the present study.

It is proposed that the signal variation curve seen across the MR images of healthy human knee cartilage obtained with the three pulse sequences used in the inventors, study arises from the water protons associated with the negatively charged anions of proteoglycans and not from those of free water nor from those associated with collagen. Therefore, the signal variation curve resembles the curve for variation in cartilage proteoglycan content (FIG. 9) because o this association.

That is, the signal variation curve appears to be related to the state, rather than the amount of water in the cartilage. Were it to be solely related to the water amount, its shape would be expected to resemble that of the water content shown in FIG. 9. Collagen tends to be more abundant at the surface than the middle of the cartilage. Thus, were the signal variation curve to be due to water associated with collagen, it would also vary in a downward sloping manner as does the collagen content shown in FIG. 9.

Water interacts with proteoglycans electrostatically, and in this respect its protons (H+) resemble cations such as $Na^+$, $Ca^{2+}$, and $Mn^{2+}$, all of which interact with the abundant anionic charges (sulfates and carboxylates) available on the sugar side chains, i.e. the acidic glycosaminoglycans (GAGs), present on the core protein chain on the proteoglycans. The cationic dyes, such as for example, toludine blue used to stain cartilage for the presence of proteoglycans also interact on the same physiochemical basis. This may explain why in the inventors' earlier experiments in the rabbit knee the decrease followed by the increase in the signal intensity was found to mirror changes in not only the biochemically measurable GAG content, but also the intensity of the toludine stain.

This explanation is consistent with the principles governing magnetic contrast relation in biological tissues. Most, if not all, the NMR signal in MR imaging comes from the protons of water rather than other organic molecules.

It is noted that load, i.e. weight-bearing, largely determines the cartilage proteoglycan content. Therefore, it is possible that deviations may be observed in the shape of signal variation curve in association with changes in the distribution of proteoglycans in situations where load is redistributed e.g., owing to immobilization, trauma, congenital dislocation of the hip, laxity of ligaments and recurrent dislocation of the patella.

Also, pixel values in MRI inherently include a certain amount of random noise. In the present study this was minimized, while preserving tissue signal contrast, by using both temporal and spatial averaging. Temporal averaging involved combining data from multiple acquisitions; spatial averaging involved combining signal intensity data from ten adjacent pixels. The operation was judged to be valid because the signal intensity profile of the ten pixels was similar. At worse, the operation could flatten the resultant signal variation curve but would not create a bell-shaped curve where one did not exist.

The magnitude of the signal intensity is known to vary according to the type of pulse sequence used, and this proved to be the case in the present study too. For example, the peak signal intensity value was found to be the highest using SE 1000/20, the lowest using the GRE, and intermediate using the SE 700/20 sequence. More importantly though, the data reveal that the shape of the signal variation curve was independent of the pulse sequence used. It was found to be bell-shaped not only using the two spin echo sequences, but also using the GRE sequence. This may be because at flip angles larger than 10°, but smaller than 90°, GRE detects a T1 weighted vector. The observed differences between the magnitude of signal intensity at the three flip angles that were used in the present study further support this explanation, since the degree of T1 weighing varies with the angle.

Cartilage comprises a mixture of collagen and proteoglycans unevenly distributed, and is organized in varying directions across the cartilage depth, which features could be responsible not only for the presence of signal intensity variations at each flip angle but also for the qualitative differences that were observed in its pattern on changing the flip angle.

Additional acquisition associated factors that might affect signal intensity include the sequence gradient magnitudes, magnet field strength, the RF pulse shape, and excitation frequency. These factors only influence signal intensity through their effects on image T1, T2, or proton density weighting and thus produce global as opposed to zonal effects within an organ.

Other technical factors potentially include, e.g., magnet and gradient inhomogeneities, partial volume, chemical shift, temperature variations, and bulk susceptibility (leading to localized magnetic field inhomogeneities) effects, all of which may lead to localized signal intensity variations.

The observed pattern o signal intensity variations within the cartilage did not vary from slice to slice making partial volume effects unlikely. Chemical shift effects occur when the structure of interest contains components of different resonant frequencies (such as lipid and water) leading to signal cancellation and misregistration. The symmetrical appearance of the signal variation curve observed in the cartilage in this study makes this unlikely as the cause of the observed bell-shaped signal intensity variations. Temperature is not a relevant factor in this isothermal environment. Finally, the physical environment of the cartilage is quite different at its periphery. For example, at its upper surface it is in contact with the joint fluid, whereas at its deeper surface it is in contact with the bone. If bulk susceptibility were a relevant factor, for example, it would be expected to produce signal intensity variations that differ between the two sides giving rise to asymmetry. The independence of signal intensity variation symmetry to pulse parameter changes further supports the conclusion that technical factors were not the cause of the signal intensity variation pattern.

Finally magnet related inhomogeneities, while localized, cause signal intensity variations over a much larger area than that as small as those examined in the present study.

These findings strongly suggest that the bell-shaped pattern of proton signal intensity across the cartilage depth is due to corresponding changes in proteoglycan concentration. To validate this hypothesis, two human cadaver patellae cartilages were imaged using a spin-echo sequence with TE/TR of 700/20 and sectioned (200 u) across their depth and proteoglycan content was measured from each slice.

As shown in FIG. 10, the patterns of the MRI signal intensity and direct proteoglycan measurement were similar and bell-shaped, which confirms that the proton signal intensity across the depth of the cartilage reflects the proteoglycan content of the tissue matrix.

This method was also tested in 7 rheumatoid arthritis patient. The mean peak proton signal intensity (SI) of medial and lateral femoral and tibial cartilages of these patients were compared with the corresponding measurement of mean peak signal intensity of 5 age and sex matched normal volunteers. These findings illustrated in FIG. 11 show a profound drop in the signal intensity measurement of both compartments, indicating that cartilage in rheumatoid arthritic knees can be differentiated from normal cartilage. A 70% (approx.) drop in RA mean peak intensity is different from the 30% (approx.) drop found in osteoarthritis (OA).

Figure 12A:
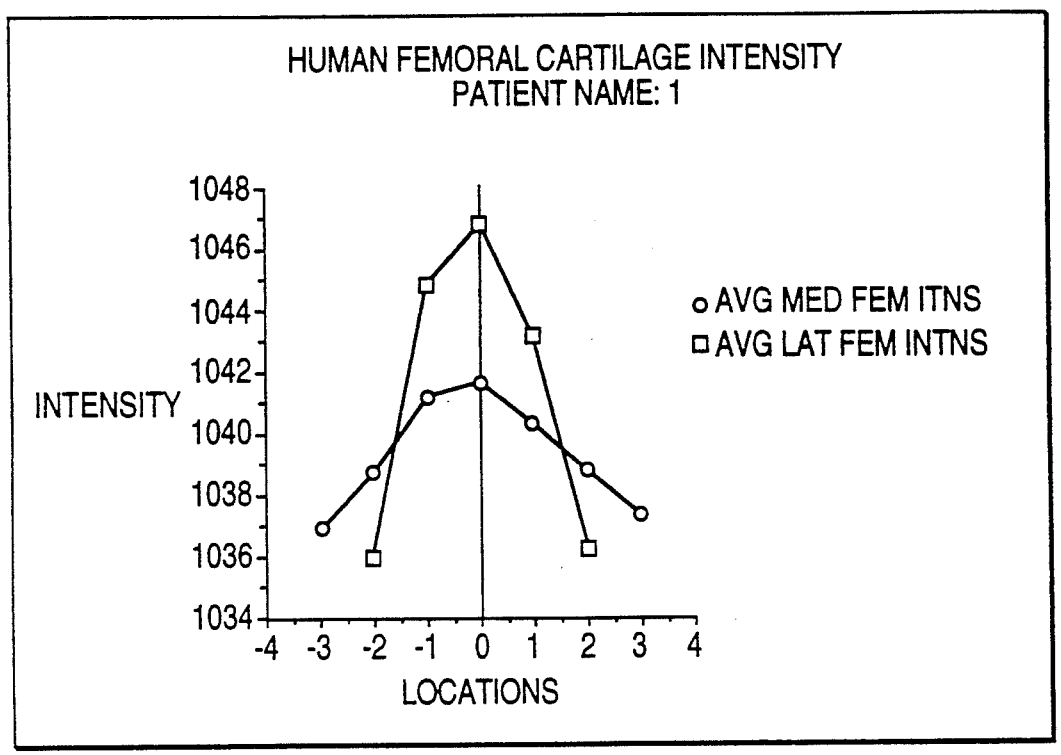
Figure 12B:
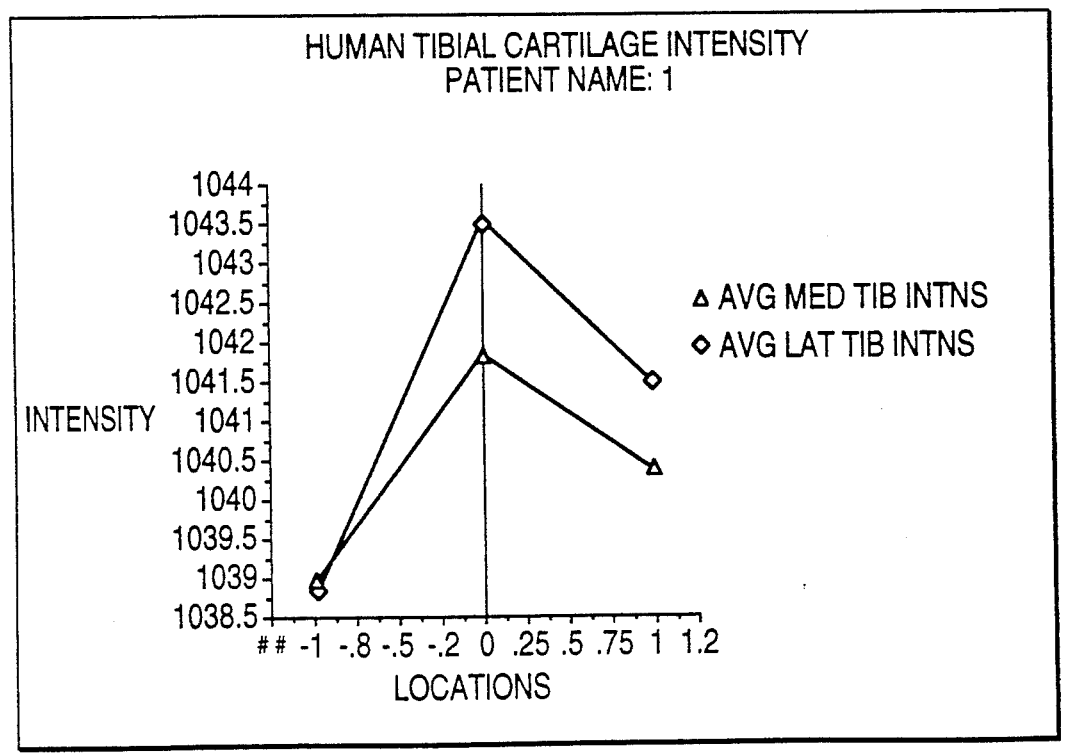
Figure 13A:
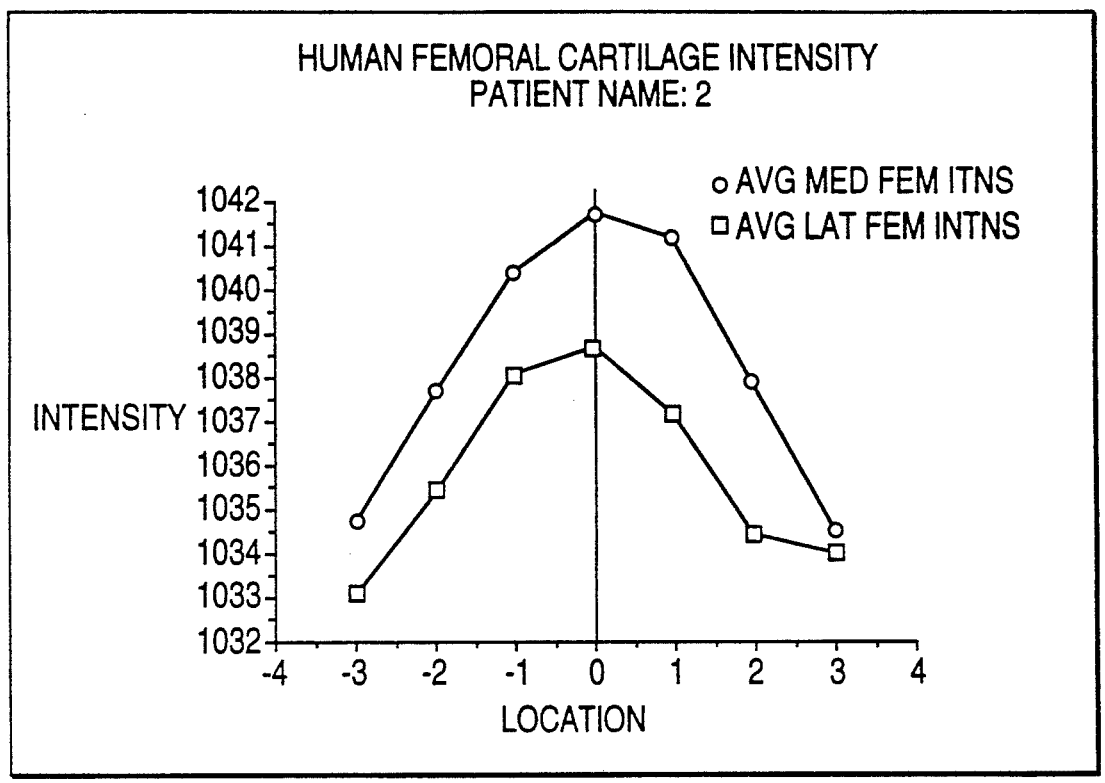
Figure 13B:
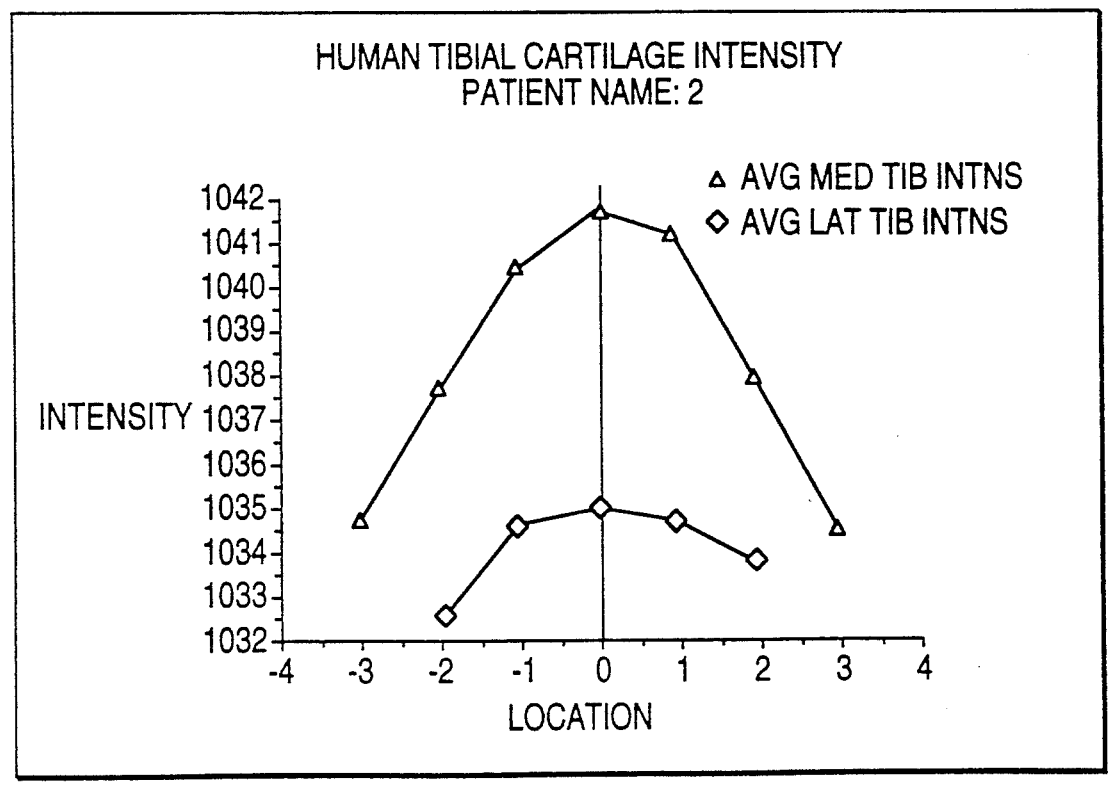
Figure 14A:
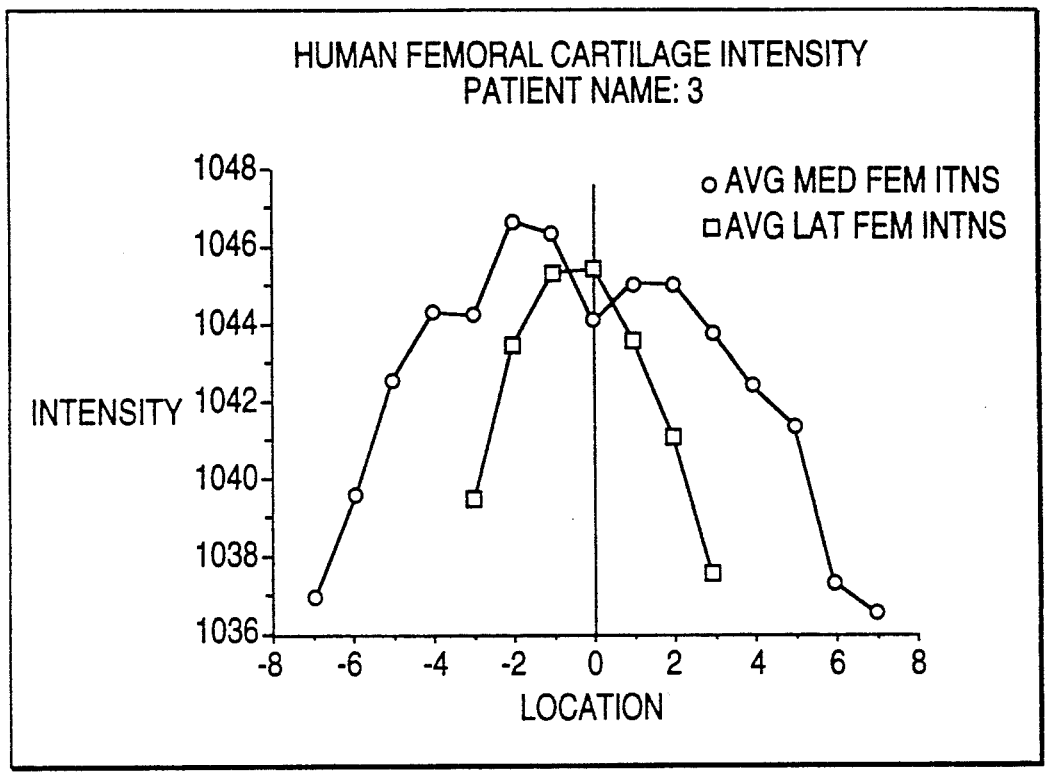
Figure 14B:
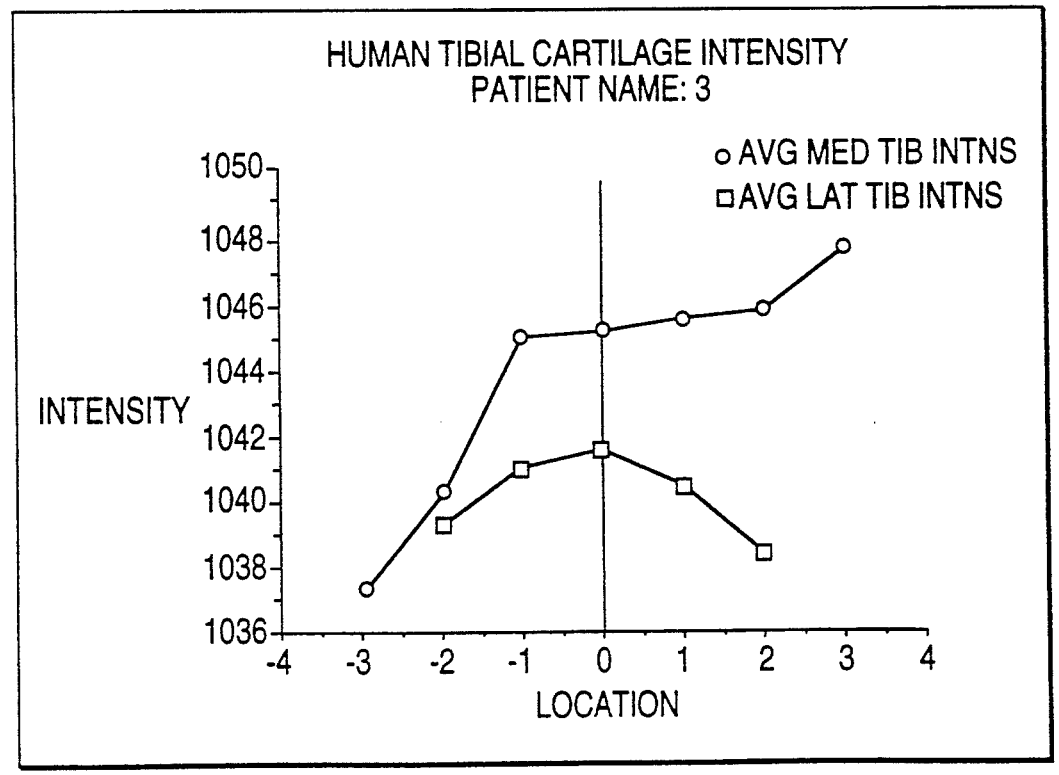
Figure 15A:
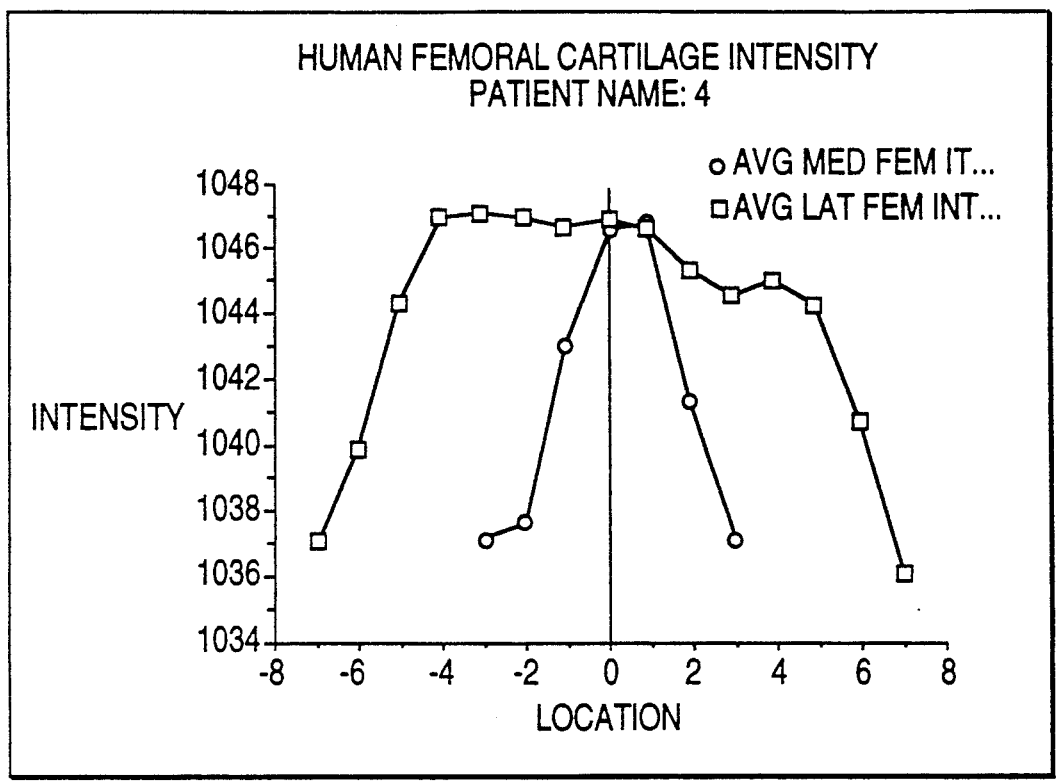
Figure 15B:
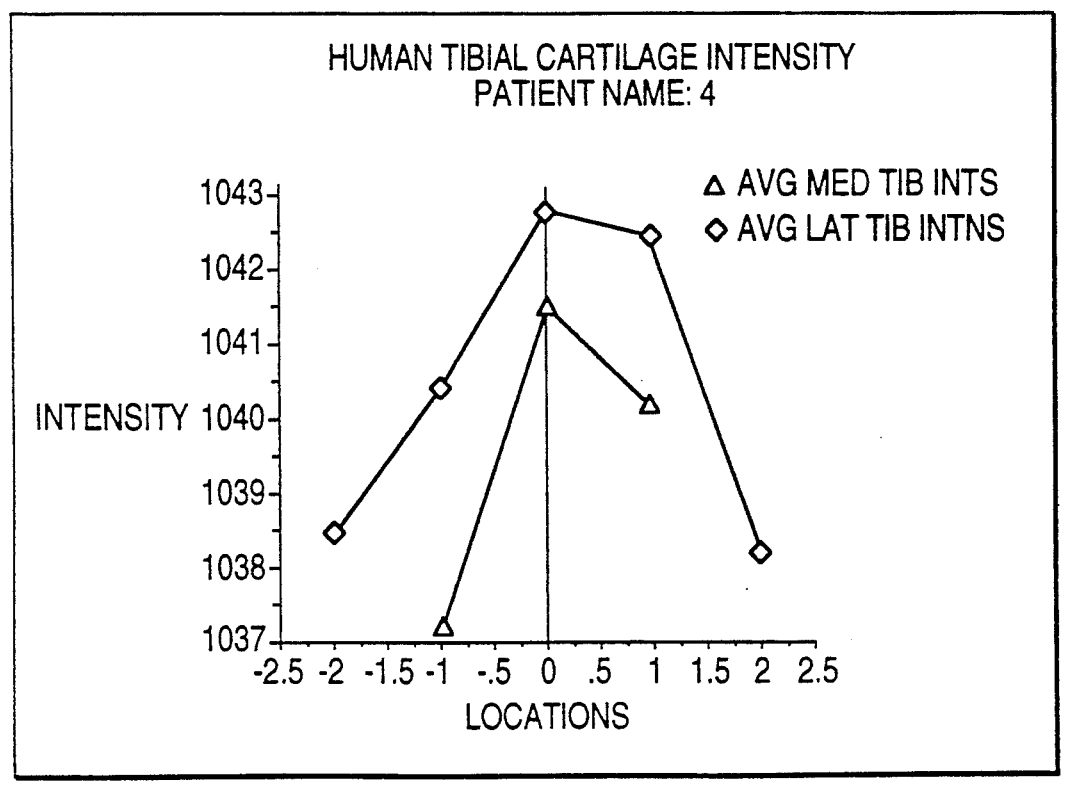
Figure 16A:
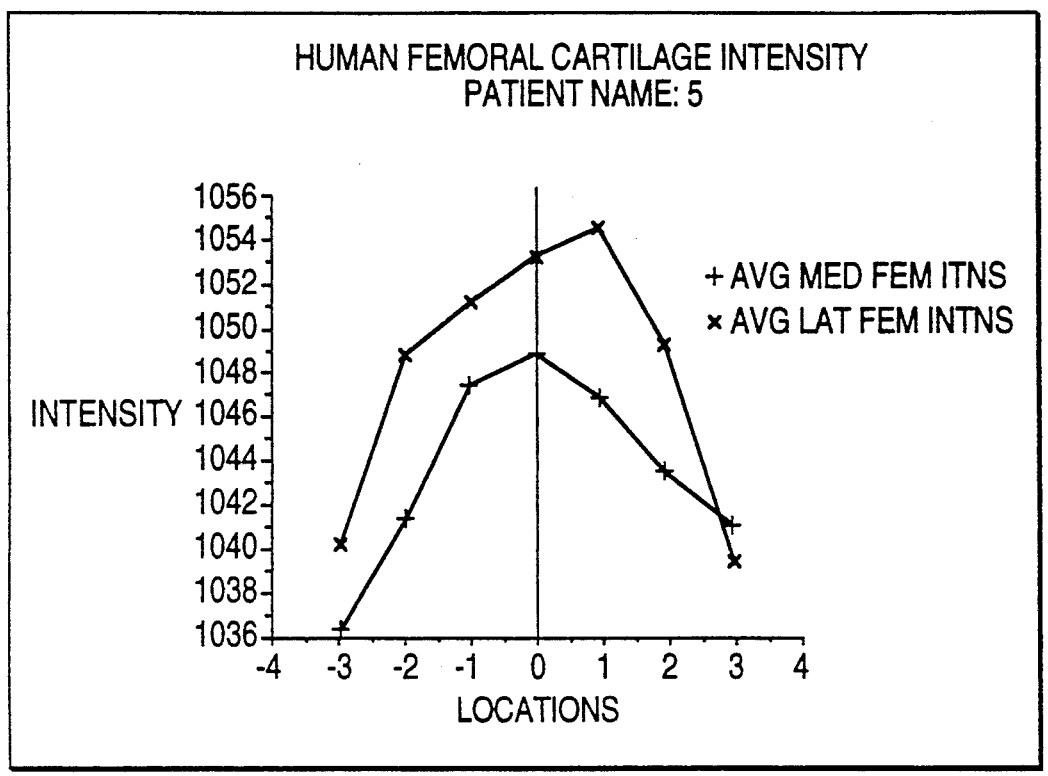
Figure 16B:
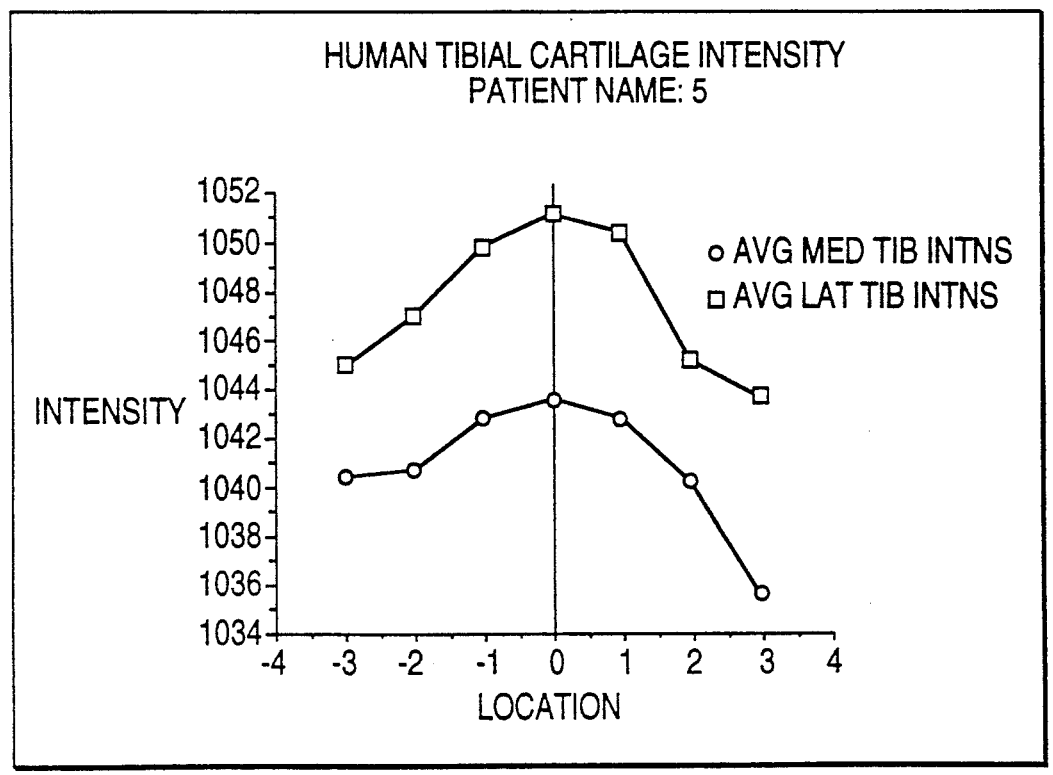
Figure 17A:
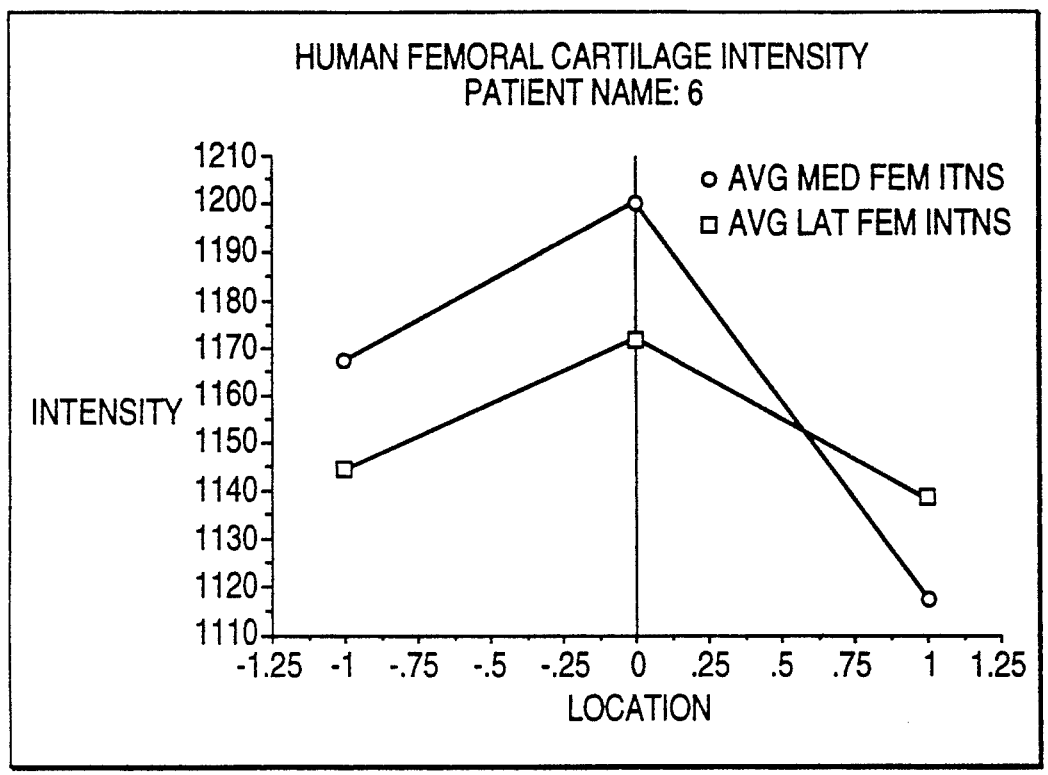
Figure 17B:
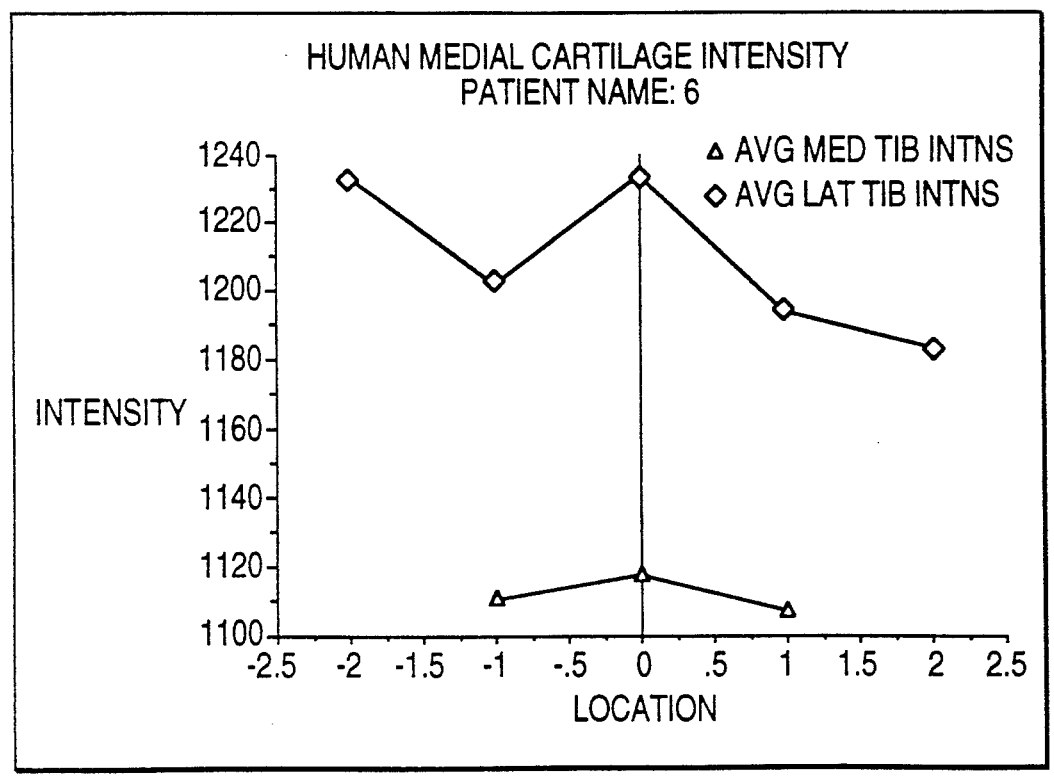
Figure 18A:
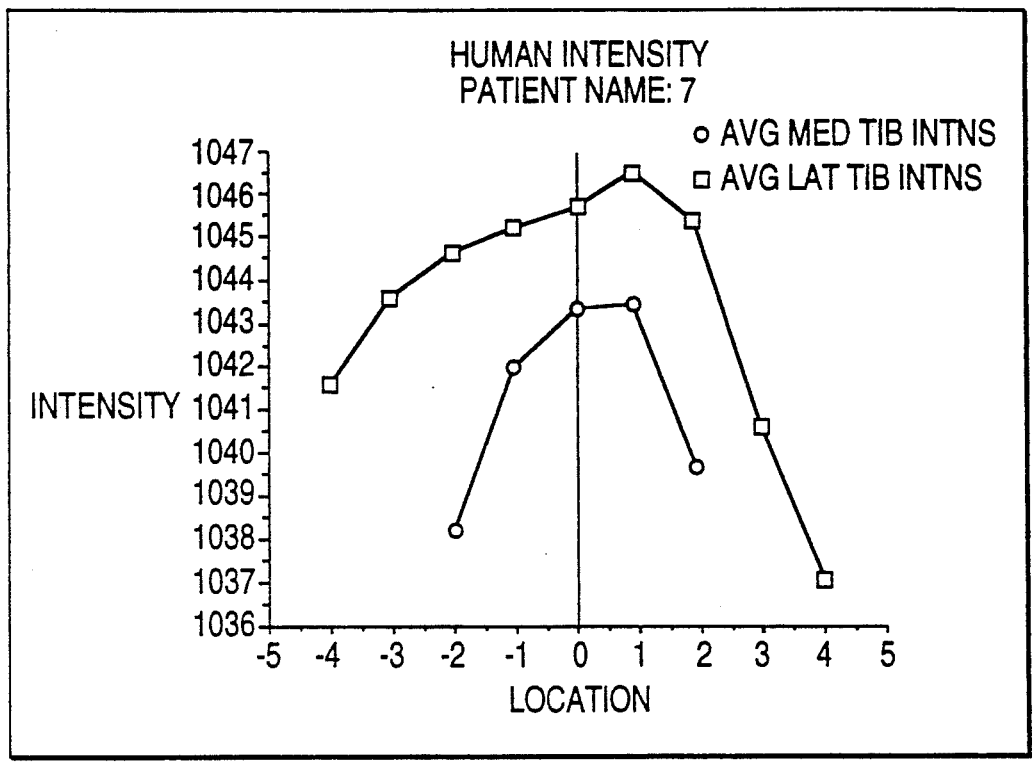
Figure 18B:
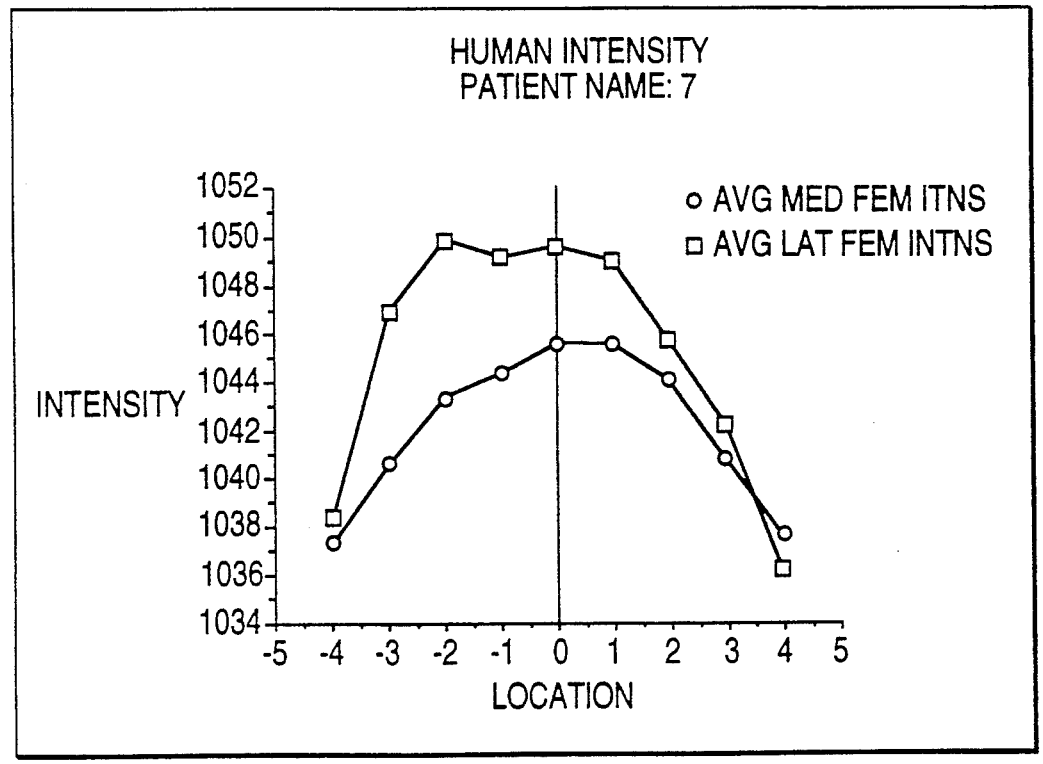

FIG. 12(a) shows the signal intensity variation pattern for the femoral cartilage of the first tested RA patient and FIG. 12 (b) shows the same for the tibial cartilage of the same patient. FIGS. 13(a) through 18(b)

are respectively for RA patients two through seven. (In FIGS. 12–18, the signal intensity numbers shown do not have a background illumination level removed, thus resulting in larger numbers than those shown in FIG. 11. The background illumination level varies according to the MRI magnet/software version employed.)

Also, it is anticipated that PG depletion in RA patients will occur more rapidly than in OA patients, which could be confirmed by conducting measurements of various patients over time to track the PG depletion rate. Thus, it is contemplated that RA could be differentiated from OA at early PG depletion stages based on a measured PG depletion rate. For example, it may be possible to differentiate RA from OA based on the amount of time during which cartilage MRI signal intensity went from a 5% drop to a 15% drop.

It is further anticipated the signal intensity patter and corresponding distribution of proteoglycan depletion will be disease specific. The techniques of the present invention can be applied to identifying such differences and so further help differentiate arthritis. For example, depending on the particular disease, proteoglycan depletion may occur diffusely across and along the cartilage, or in a spotty random-like manner, or in a localized manner.

In summary, progression of arthritis is characterized by degradation of the articular cartilage. The cartilage loss is initiated by a loss of proteoglycan. The present inventor's have discovered that PG depletion may be detected by the magnetic resonance (MR) proton signal intensity measurements using the present method. Thus, a significant drop in signal intensity is indicative of the loss of proteoglycan.

In conclusion, the present inventors have discovered a novel method of diagnosing PG depletion in articular cartilage, based upon a correlation between the signal intensity of NMR images of the cartilage and its PG content. Since PG depletion is a precursor to cartilage degeneration, this method provides a very useful means for diagnosing a potential cartilage degeneration in a patient so that preventive measures may be taken if necessary.

Also, the techniques of the present invention can be applied to track the progression or remission of proteoglycan depletion in a patient. That is, by monitoring the MRI signal intensity of a patient's articular cartilage over time, an increase or decrease in proteoglycan of that cartilage can be diagnosed. Such would be particularly useful in testing the effectiveness of therapeutic drugs intended to halt proteoglycan depletion and/or replenish proteoglycan content. For example, by comparing MRI signal intensities of cartilage before and after drug administration, an indication of the drug's effectiveness can be obtained.

We claim:

1. A non-invasive method of diagnosing a proteoglycan deficiency in cartilage comprising the steps of quantifying a signal intensity of a magnetic resonance image of the cartilage and correlating the thus quantified signal intensity with at least one predetermined reference signal intensity indicative of a predetermined cartilage proteoglycan content.

2. A method as recited in claim 1, wherein the signal intensity is quantified as a gray-scale pixel illumination of the magnetic resonance image.

3. A method as recited in claim 1, wherein the signal intensity of the magnetic resonance image is quantified on a pixel-by-pixel basis across a depth of the cartilage.

4. A method as recited in claim 3, wherein the signal intensity is quantified as a gray-scale pixel illumination of the magnetic resonance image.

5. A method as recited in claim 3, wherein said correlating step includes comparing a maximum quantified signal intensity along the depth of the cartilage with the at least one predetermined reference signal intensity.

6. A method as recited in claim 5, wherein the signal intensity is quantified as a gray-scale pixel illumination of the magnetic resonance image.

7. A method as recited in claim 3, wherein said quantifying step includes determining, for each representative pixel location of the magnetic resonance image across the depth of the cartilage, a mean signal intensity of plural pixels extending in a direction traversing a depth direction of the cartilage.

8. A method as recited in claim 7, wherein said correlating step includes comparing a maximum mean signal intensity from among the representative pixel locations along the depth of the cartilage with the at least one predetermined reference signal intensity.

9. A method as recited in claim 8, wherein the signal intensity is quantified as a gray-scale pixel illumination of the magnetic resonance image.

10. A method as recited in claim 7, wherein said correlating step includes comparing a pattern illustrating the mean signal intensity for each representative pixel location across the depth of the cartilage with at least one predetermined reference signal intensity pattern.

11. A method as recited in claim 10, wherein the signal intensity is quantified as a gray-scale pixel illumination of the magnetic resonance image.

12. A non-invasive method of diagnosing a proteoglycan deficiency in cartilage comprising quantifying a signal intensity of a magnetic resonance image of the cartilage and plotting the thus quantified signal intensity of the magnetic resonance image of the cartilage versus a depth of the cartilage to obtain a signal intensity patter, the thus obtained signal intensity pattern being indicative of proteoglycan concentration and distribution across the depth of the cartilage, and then comparing a peak signal intensity of the signal intensity pattern with at least one predetermined reference signal intensity indicative of a predetermined cartilage proteoglycan content.

13. A method as recited in claim 12, wherein the signal intensity is quantified as a gray-scale pixel illumination of the magnetic resonance image for pixels of the magnetic resonance image extending across the depth of the cartilage.

14. A non-invasive method of diagnosing a proteoglycan deficiency in cartilage comprising quantifying a signal intensity of each of plural magnetic resonance slice images of plural regions of the cartilage and plotting for each region the thus quantified signal of the magnetic resonance image of the cartilage versus a depth of the cartilage to obtain a signal intensity pattern for each region, the thus obtained signal intensity pattern being indicative of proteoglycan concentration and distribution across the depth of the cartilage, and then comparing a peak signal intensity of the signal intensity pattern with at least one predetermined reference signal intensity indicative of a predetermined cartilage proteoglycan content.

15. A method as recited in claim 14, wherein said quantifying includes quantifying a signal intensity of each of medial and lateral condyles of articular cartilage.

16. A method as recited in claim 14, wherein the signal intensity is quantified as a gray-scale pixel illumination of the magnetic resonance image for pixels of the magnetic resonance image extending along the depth of the cartilage.

17. A non-invasive method of tracking the progression and remission of proteoglycan depletion in cartilage, comprising the steps of quantifying a signal intensity of each of plural magnetic resonance images of the cartilage taken in succession over time, and comparing the thus quantified signal intensities of the plural magnetic resonance images of the cartilage with one another, wherein a decrease over time in the quantified signal intensities is indicative of a decrease in proteoglycan content and an increase over time in the quantified signal intensities is indicative of a increase in proteoglycan content.

18. A method as recited in claim 17, wherein the signal intensity is quantified as a gray-scale pixel illumination of the magnetic resonance images for pixels of the magnetic resonance images extending across the depth of the cartilage.

19. A non-invasive method of assessing the effectiveness of a therapeutic drug intended to cease or prohibit proteoglycan depletion in cartilage comprising the steps of quantifying a signal intensity of each of plural magnetic resonance images of the cartilage taken in succession over time before and after administration of the therapeutic drug, and comparing the thus quantified signal intensities of the plural magnetic resonance images of the cartilages with one another, wherein a decrease over time in the quantified signal intensities is indicative of a decrease in proteoglycan content and an increase in the quantified signal intensities is indicative of an increase over time in proteoglycan content.

20. A method as recited in claim 19, wherein the signal intensity is quantified as a gray-scale pixel illumination of the magnetic resonance images for pixels of the magnetic resonance images extending across the depth of the cartilage.

21. A non-invasive method of diagnosing an arthritic joint comprising the steps of quantifying a signal intensity of a magnetic resonance image of an articular cartilage of the joint and correlating the thus quantified signal intensity with a predetermined reference signal intensity indicative of normal proteoglycan content of the articular cartilage, wherein a substantial decrease in the quantified signal intensity relative to the reference signal intensity is indicative of an arthritic joint.

22. A method as recited in claim 21, wherein the signal intensity is quantified as a gray-scale pixel illumination of the magnetic resonance image for pixels of the magnetic resonance image extending across the depth of the cartilage.

23. A non-invasive method of indicating a proteoglycan content in cartilage comprising quantifying a signal intensity of a magnetic resonance image of the cartilage and plotting the thus quantified signal intensity of the magnetic resonance image of the cartilage versus a depth of the cartilage to obtain a signal intensity pattern, the thus obtained signal intensity pattern being indicative of proteoglycan concentration and distribution across the depth of the cartilage.

24. A non-invasive method of indicating a proteoglycan content in cartilage comprising quantifying a signal intensity of each of plural magnetic resonance slice images of plural regions of the cartilage and plotting for each region and thus quantified signal of the magnetic resonance image other cartilage versus a depth of the cartilage to obtain a signal intensity pattern for each region, the thus obtained signal intensity patterns being indicative of a proteoglycan concentration and distribution across the depth of the cartilage.

* * * * *